United States Patent
Shih et al.

(10) Patent No.: US 8,741,663 B2
(45) Date of Patent: *Jun. 3, 2014

(54) ENHANCED DETECTION SENSITIVITY WITH PIEZOELECTRIC SENSORS

(75) Inventors: Wan Y. Shih, Bryn Mawr, PA (US); Wei-Heng Shih, Bryn Mawr, PA (US); Qing Zhu, San Jose, CA (US)

(73) Assignee: Drexel University, Philadelphia, PA (US)

(*) Notice: Subject to any disclaimer, the term of this patent is extended or adjusted under 35 U.S.C. 154(b) by 627 days.

This patent is subject to a terminal disclaimer.

(21) Appl. No.: 12/921,756

(22) PCT Filed: Mar. 4, 2009

(86) PCT No.: PCT/US2009/036048
§ 371 (c)(1),
(2), (4) Date: Oct. 20, 2010

(87) PCT Pub. No.: WO2009/126378
PCT Pub. Date: Oct. 15, 2009

(65) Prior Publication Data
US 2011/0124124 A1 May 26, 2011

Related U.S. Application Data

(60) Provisional application No. 61/035,669, filed on Mar. 11, 2008.

(51) Int. Cl.
*G01N 33/551* (2006.01)

(52) U.S. Cl.
USPC ........... 436/524; 436/501; 436/518; 436/149; 435/7.1; 435/283.1; 435/287.2

(58) Field of Classification Search
USPC ........ 436/524, 501, 518, 149; 435/7.1, 283.1, 435/287.2
See application file for complete search history.

(56) References Cited

U.S. PATENT DOCUMENTS

| 3,205,464 A | 9/1965 | Schwartz |
| 4,093,883 A | 6/1978 | Yamamoto |

(Continued)

FOREIGN PATENT DOCUMENTS

| EP | 0631319 A1 | 12/1994 |
| EP | 1536227 A2 | 6/2005 |

(Continued)

OTHER PUBLICATIONS

Amanuma, K. et al., "Crystallization behavior of sol-gel derived Pb(Zr,Ti)O3 thin films and the polarization switching effect on film microstructure", Appl. Phys. Lett., 65(24): 3140-3142 (1994).

(Continued)

*Primary Examiner* — Melanie Y Brown
(74) *Attorney, Agent, or Firm* — Mendelsohn, Drucker & Dunleavy, P.C.

(57) ABSTRACT

A method for enhancing the detection sensitivity of a piezoelectric microcantilever sensor. The method may involve providing a piezoelectric microcantilever and inducing a change in the Young's modulus during detection of a species of interest. The change in the Young's modulus may be induced or enhanced by the application of a DC bias electric field to the piezoelectric layer that enhances non-180° polarization domain switching of the piezoelectric layer. The change in the Young's modulus may also result from binding of the species of interest to the piezoelectric microcantilever sensor or a combination of binding and application of a DC bias electric field Significantly enhanced detection sensitivity results from the changed Young's modulus of the piezoelectric layer.

22 Claims, 11 Drawing Sheets

(56) References Cited

U.S. PATENT DOCUMENTS

| | | | |
|---|---|---|---|
| 4,302,694 A | 11/1981 | Fujishima et al. |
| 4,349,762 A | 9/1982 | Kitamura et al. |
| 4,363,993 A | 12/1982 | Nishigaki et al. |
| 4,403,166 A | 9/1983 | Tanaka et al. |
| 4,528,502 A | 7/1985 | Rocha |
| 4,649,312 A | 3/1987 | Robin et al. |
| 4,802,371 A | 2/1989 | Calderara et al. |
| RE33,691 E | 9/1991 | Harnden, Jr. et al. |
| 5,054,323 A | 10/1991 | Hubbard et al. |
| 5,313,535 A | 5/1994 | Williams |
| 5,334,835 A | 8/1994 | Nakayama et al. |
| 5,338,999 A | 8/1994 | Ramakrishnan et al. |
| 5,382,864 A | 1/1995 | Morikawa |
| 5,445,008 A | 8/1995 | Wachter et al. |
| 5,475,318 A | 12/1995 | Marcus et al. |
| 5,501,986 A | 3/1996 | Ward et al. |
| 5,503,010 A | 4/1996 | Yamanaka |
| 5,553,486 A | 9/1996 | Bonin |
| 5,626,728 A | 5/1997 | Ramakrishnan et al. |
| 5,689,063 A | 11/1997 | Fujiu et al. |
| 5,719,324 A | 2/1998 | Thundat et al. |
| 5,780,727 A | 7/1998 | Gimzewski et al. |
| 5,807,758 A | 9/1998 | Lee et al. |
| 5,866,807 A | 2/1999 | Elings et al. |
| 5,874,126 A | 2/1999 | Kahn et al. |
| 5,948,993 A | 9/1999 | Ting et al. |
| 5,966,787 A | 10/1999 | Nakayama et al. |
| 5,996,412 A | 12/1999 | Hansen |
| 6,075,585 A | 6/2000 | Minne et al. |
| 6,278,379 B1 | 8/2001 | Allen et al. |
| 6,280,396 B1 | 8/2001 | Clark |
| 6,289,717 B1 | 9/2001 | Thundat et al. |
| 6,336,366 B1 | 1/2002 | Thundat et al. |
| 6,422,069 B1 | 7/2002 | Shimizu et al. |
| 6,458,327 B1 | 10/2002 | Vossmeyer et al. |
| 6,465,368 B2 | 10/2002 | Inoue et al. |
| 6,579,726 B1 | 6/2003 | Natan et al. |
| 6,589,727 B1 | 7/2003 | Klenerman et al. |
| 6,621,080 B2 | 9/2003 | Yamamoto |
| 6,734,425 B2 | 5/2004 | Hantschel et al. |
| 6,763,705 B1* | 7/2004 | Thundat et al. ............... 73/64.53 |
| 6,781,285 B1 | 8/2004 | Lazarus et al. |
| 6,903,491 B2 | 6/2005 | Irie et al. |
| 6,992,421 B2 | 1/2006 | Ikeda et al. |
| 7,022,540 B2 | 4/2006 | Kim et al. |
| 7,055,378 B2 | 6/2006 | Su et al. |
| 7,083,270 B2 | 8/2006 | Torii et al. |
| 7,084,554 B2 | 8/2006 | Xu et al. |
| 7,104,134 B2 | 9/2006 | Amano et al. |
| 7,195,909 B2 | 3/2007 | Klenerman et al. |
| 7,252,004 B2 | 8/2007 | Fink et al. |
| 7,263,874 B2 | 9/2007 | Fitch et al. |
| 7,305,883 B2* | 12/2007 | Khuri-Yakub et al. ......... 73/579 |
| 7,413,341 B1 | 8/2008 | Kachynski et al. |
| 7,458,265 B2 | 12/2008 | Shih et al. |
| 7,476,513 B2 | 1/2009 | Murphy et al. |
| 7,497,133 B2 | 3/2009 | Shih et al. |
| 7,521,257 B2 | 4/2009 | Adams et al. |
| 7,744,713 B2 | 6/2010 | Blessing |
| 7,744,773 B2 | 6/2010 | Shih |
| 7,779,709 B2 | 8/2010 | Roney, Jr. et al. |
| 7,942,056 B2 | 5/2011 | Mutharasan et al. |
| 7,992,431 B2 | 8/2011 | Shih et al. |
| 8,033,185 B2 | 10/2011 | Shih et al. |
| 8,241,569 B2 | 8/2012 | Shih et al. |
| 8,481,335 B2 | 7/2013 | Shih et al. |
| 8,496,870 B2 | 7/2013 | Shih et al. |
| 2002/0094528 A1 | 7/2002 | Salafsky |
| 2002/0117659 A1 | 8/2002 | Lieber et al. |
| 2002/0155303 A1 | 10/2002 | Wielstra et al. |
| 2003/0032293 A1 | 2/2003 | Kim et al. |
| 2003/0068655 A1 | 4/2003 | Bottomley et al. |
| 2003/0194697 A1 | 10/2003 | Klenerman et al. |
| 2003/0224551 A1 | 12/2003 | Kim et al. |
| 2003/0235681 A1 | 12/2003 | Sebastian et al. |
| 2004/0022677 A1 | 2/2004 | Wohlstadter et al. |
| 2004/0023413 A1 | 2/2004 | Opalsky |
| 2004/0265664 A1 | 12/2004 | Badding et al. |
| 2005/0112621 A1 | 5/2005 | Kim et al. |
| 2005/0114045 A1 | 5/2005 | Giurgiutiu et al. |
| 2005/0199047 A1 | 9/2005 | Adams et al. |
| 2005/0252295 A1 | 11/2005 | Fink et al. |
| 2005/0277852 A1 | 12/2005 | Shih et al. |
| 2005/0287680 A1 | 12/2005 | Venkatasubbarao et al. |
| 2006/0053870 A1 | 3/2006 | Berndt |
| 2006/0125489 A1* | 6/2006 | Feucht et al. ................. 324/633 |
| 2006/0160134 A1 | 7/2006 | Melker et al. |
| 2006/0217893 A1 | 9/2006 | Li et al. |
| 2006/0223691 A1 | 10/2006 | Shih et al. |
| 2006/0228657 A1 | 10/2006 | Masters et al. |
| 2006/0257286 A1 | 11/2006 | Adams |
| 2007/0089515 A1 | 4/2007 | Shih et al. |
| 2007/0141721 A1 | 6/2007 | Vafai et al. |
| 2007/0169553 A1 | 7/2007 | Mutharasan et al. |
| 2007/0218534 A1 | 9/2007 | Klenerman et al. |
| 2008/0034840 A1 | 2/2008 | Mutharasan |
| 2008/0035180 A1 | 2/2008 | Mutharasan |
| 2008/0131867 A1 | 6/2008 | Meiri |
| 2008/0138797 A1* | 6/2008 | Hunt et al. ....................... 435/6 |
| 2009/0007645 A1 | 1/2009 | Shih et al. |
| 2009/0053709 A1 | 2/2009 | Mutharasan |
| 2009/0078023 A1 | 3/2009 | Mutharasan |
| 2009/0145246 A1 | 6/2009 | Shih et al. |
| 2009/0203000 A1 | 8/2009 | Mutharasan |
| 2010/0068697 A1 | 3/2010 | Shih et al. |
| 2010/0088039 A1 | 4/2010 | Yang et al. |
| 2010/0170342 A1 | 7/2010 | Sinkus et al. |
| 2010/0224818 A1 | 9/2010 | Shih et al. |
| 2010/0239463 A1 | 9/2010 | Shih et al. |
| 2010/0281962 A1 | 11/2010 | Shih et al. |
| 2011/0172565 A1 | 7/2011 | Shih et al. |
| 2011/0265227 A1 | 10/2011 | Shih et al. |
| 2012/0053489 A1 | 3/2012 | Shih et al. |

FOREIGN PATENT DOCUMENTS

| | | |
|---|---|---|
| JP | 3093849 B2 | 4/2000 |
| JP | 2003-298131 A | 10/2003 |
| JP | 2004-265899 A | 9/2004 |
| JP | 2007-67125 A | 3/2007 |
| WO | 98/50773 A2 | 11/1998 |
| WO | 2004/061991 A1 | 7/2004 |
| WO | 2005/043126 * | 5/2005 |
| WO | 2005/043126 A2 | 5/2005 |
| WO | WO2005084191 A2 | 9/2005 |
| WO | 2006/031072 A1 | 3/2006 |
| WO | 2007/087328 A2 | 8/2007 |
| WO | WO 2007/109228 A1 | 9/2007 |
| WO | 2007/133619 A1 | 11/2007 |
| WO | 2008/020903 A2 | 2/2008 |
| WO | 2008/021187 A2 | 2/2008 |
| WO | 2008/021189 A2 | 2/2008 |
| WO | 2008/101199 A1 | 8/2008 |
| WO | 2009/014830 A1 | 1/2009 |
| WO | 2009/035732 A2 | 3/2009 |
| WO | 2009/035732 A3 | 3/2009 |
| WO | 2009/046251 A2 | 4/2009 |
| WO | WO2010055959 A1 | 5/2010 |

OTHER PUBLICATIONS

Ammari, H. et al., "T-Scan Electrical Impedance Imaging System for Anomaly Detection", Siam J. Appl. Math., 65(1): 252-266 (2004).

Baselt, D. R. et al., "Biosensor based on force microscope technology", J. Vac. Sci. Technol. B, 14(2): 789-793 (1996).

Birnie, III, D. P. et al., "Coating uniformity and device applicability of spin coated sol-gel PXT films", Microelectronic Engineering, 29: 189-192 (1995).

Bondoux, C. et al., "MgO insulating films prepared by sol-gel route for SiC substrate", J. Europe. Ceramic Soc., 25: 2795-2798 (2005).

Brito, R. et al., "Adsorption of 3-mercaptopropyltrimethoxysilane and 3-aminopropyltrimethoxysilane at platinum electrodes", J. Electroanalytical Chem., 520: 47-52 (2002).

(56) References Cited

OTHER PUBLICATIONS

Capobianco, J. A., et al., "Methltrimethoxysilane- insulated piezoelectric microcantilevers for direct, all-electrical biodetection in buffered aqueous solutions", Rev. Sci. Instrum., 77: 125105-1-125105-6 (2006).

Capobianco, J. A., et al., "3-mercaptopropyltrimethoxysilane as insulating coating and surface for protein immobilization for piezoelectric microcantilever sensors", Rev. Sci. Instrum., 78: 046106-1-046106-3 (2007).

Carlier, S. G., et al., "Elastography", J. Cardiovasc Risk, 9(5): 237-245 (2002).

Che, G. et al., "Molecular recognition based on (3-mercaptopropyl) trimethoxysilane modified gold electrodes", J. Electroanalytical Chem., 417: 155-161 (1996).

Chen, G. Y. et al., "Adsorption-induced surface stress and its effects on resonance frequency of microcantilevers", J. Appl. Phys., 77(8): 3618-3622 (1995).

Chen, X. et al., "Electrochemical and Spectroscopic Characterization of Surface Sol-Gel Processes", Langmuir, 20 (20): 8762-8767 (2004).

Cho, S. H. et al., "Micro-scale metallization on flexible polyimide substrate by Cu electroplating using SU-8 photoresist mask", Thin Solid Films, 475: 68-71 (2005).

Duval, F.F.C. et al., "Stable TiO2/Pt electrode structure for lead containing ferroelectric thick films on silicon MEMS structures", Thin Solid Films, 444: 235-240 (2003).

Feili, D. et al., "Encapsulation of organic field effect transistors for flexible biomedical microimplants", Sensors and Actuators, A120: 101-109 (2005).

Ferrini, R. et al., "Screening Mammography for Breast Cancer: American College of Preventive Medicine Practice Policy Statement", www.acpm.org/breast, pp. 1-4 (2005).

Fritz, J. et al., "Translating Biomolecular Recognition into Nanomechanics", Science, 288: 316-318 (2000).

Fung, Y. S. et al., "Self-Assembled Monolayers as the Coating in a Quartz Piezoelectric Crystal Immunosensor to Detect *Salmonella* in Aqueous Solution", Anal. Chem., 73: 5302-5309 (2001).

Gao, L. et al., "Imaging of the elastic properties of tissue: A review", Ultrasound in Med. & Biol., 22(8): 959-977 (1996). Abstract Only.

Greenleaf, J. F. et al., "Selected Methods for Imaging Elastic Properties of Biological Tissues", Annu. Rev. Biomed. Eng., 5: 57-78 (2003).

Gu, H. et al., "Single-Calcination Synthesis of Pyrochlore-Free 0.9Pb(Mg1/3Nb2/3)O3-0.1PbTiO3 and Pb (Mg1/3Nb2/3)O3 Ceramics Using a Coating Method", J. Am. Ceram. Soc., 86(2): 217-221 (2003).

Haccart, T. et al., "Evaluation of niobium effects on the longitudinal piezoelectric coeffecients of Pb(Zr,Ti)O3 thin films", Appl. Phys. Lett., 76(22): 3292-3294 (2000).

Han, W. et al., "A magnetically driven oscillating probe microscope for operations in liquids", Appl. Phys. Lett., 69(26): 4111-4113 (1996).

Hiboux, S. et al., "Mixed titania-lead oxide seed layers for PZT growth on Pt(111): a study on nucleation, texture and properties", J. Europe. Ceram. Soc., 24: 1593-1596 (2004).

Hwang, I.H. et al., "Self-actuating biosensor using a piezoelectric cantilever and its optimization", Journal of Physics: Conference Series 34, pp. 362-367, 2006.

Hwang, K.S. et al., "In-situ quantitative analysis of a prostate-specific antigen (PSA) using a nanomechanical PZT cantilever", Lab Chip, 4: 547-552 (2004).

Ilic, B. et al., "Mechanical resonant immunospecific biological detector", Appl. Phys. Lett., 77(3): 450-452 (2000).

Itoh, T. et al., "Self-excited force-sensing microcantilevers with piezoelectric thin films for dynamic scanning force microscopy", Sensor and Actuators, A54:477-481 (1996).

Jung, S.K. et al., "Polymeric Marcaptosilane-Modified Platinum Electrodes for Elimination of Interferants in Glucose Biosensors", Anal. Chem., 68: 591-596 (1996).

Kanda, T. et al., "A flat type touch probe sensor using PZT thin film vibrator", Sensors and Actuators, 83: 67-75 (2000).

Katiyar, P. et al. "Electrical properties of amorphous aluminum oxide thin films", Acta Materialia, 53: 2617-2622 (2005).

Keller, A. et al., "Reliability of Computed Tomography Measurements of Paraspinal Muscle Cross-Sectional Area and Density in Patients With Chronic Low Back Pain", Spine, 28(13): 1455-1460 (2003).

Kelly, J. et al., "Effect of Composition on the Electromechanical Properties of (1-x)Pb(Mg1/3Nb2/3)O3-xPbTiO3 Ceramics" J. Am. Ceram. Soc., 80(4): 957-964 (1997).

Khabari, A. et al., "Partially ionized beam deposition of parylene" J. Non-Crystalline Solids, 351: 3536-3541 (2005).

Kim, S.H. et al., "Influence of Al2O3 diffusion barrier and PbTiO3 seed layer on microstructural and ferroelectric charachteristics of PZT thin films by sol-gel spin coating method," Thin Solid Films, 305: 321-326 (1997).

Kim, S.J. et al., "Fabrication and Characterization of Pb(Zr,Ti)O3 Microcantilever for Resonance Sensors," Jpn. J. Appl. Phys., 42(3): 1475-1478 (2003).

Klissurska, R.D. et al. "Microstructure of PZT sol-gel films on Pt substrates with different adhesion layers," Microelectronic Engineering, 29: 297-300 (1995).

Kruse, S.A. et al., "Tissue characterization using magnetic resonance elastography: preliminary results," Phys. Med. Biol., 45: 1579-1590 (2000).

Kumar, V. et al., "A Simple System for the Preparation of Submicrometer Lead Titanate Powders by the Sol-Gel Method," J. Am. Ceram. Soc., 79(10): 2775-2778 (1996).

Kwok, CLK. et al., "Low temperature perovskite formation of lead zirconate titanate thin films by a seeding process," J. Mater. Res., 8(2): 339-344 (1993).

H. Zhang, et al., "A Sensitive and High-Throughput Assay to Detect Low-Abundance Proteins in Serum," Nature Medicine 12(4) 473-477 (2006).

J. W. Park, S. Kurosawa, H. Aizawa Y. Goda, M. Takai and K. Ishihara, "Piezoelectric Immunosensor for Bisphenol A Based on Signal Enhancing Step With 2-methacrolyloxyethyl Phosphorylcholine Polymeric Nanoparticle," Analyst, 131, 155-162 (2006).

A. M. Smith, G. Ruan, M. N. Rhyner, and S. Nie, "Engineering Luminescent Quantum Dots for In Vivo Molecular and Cellular Imaging," Ann. Biomed. Eng., 34 (1),3-14 (2006).

R. E. Jaeger and L. Egerton, "Hot-Pressing of Potassium-Sodium Niobates," J. Am. Ceram. Soc. 45, 209 (1962).

H. Birol, D. Damjanovic and N. Setter, "Preparation and Characterization of (K0.5Na0.5)NbO3 Ceramics", J. Eur. Ceram. Soc. 26, 861 (2006).

Y. Guo, K. Kakimoto, and H. Ohsato, "Phase Transitional Behavior and Piezoelectric Properties of (Na0.5K0.5)NbO3—LiNbO3 Ceramics," Appl. Phys. Lett., 85, 4121 (2004).

Y. Guo, K. Kakimoto, and H. Ohsato, "(Na0.5K0.5)NbO3—LiTaO3 Lead-free Piezoelectric Ceramics," Mater. Lett., 59, 241 (2005).

H. Li, W.Y. Shih, and W.-H. Shih, "Effect of Antimony Concentration on the Crystalline Structure, Dielectric and Piezoelectric Properties of (Na0.5K0.5)0.945Li0.055Nb1—xSbxO3 Solid Solutions", J. Am. Ceram. Soc., 90, 3070 (2007).

S. Zhang, R. Xia, T. R. Shrout, J. Zang, and J. Wang, "Piezoelectric Properties in Perovskite 0.948(K0.5Na0.5)NbO3-0.052LiSbO3 lead-free ceramics", J. App. Phys., 100, 104108 (2006).

X. Li, W. Y. Shih, J. S. Vartuli, D. L. Milius, I. A. Aksay, and W.-H. Shih, "Effect of Transverse Tensile Stress on Electric-Field-Induced Domain Reorientation in Soft PZT: In Situ XRD Study", J. Am. Ceram. Soc. 85 (4), 844 (2002).

Q. Zhu, W. Y. Shih, and W.-H. Shih, "Real-Time, Label-Free, All-Electrical Detection of *Salmonella typhimurium* Using Lead Titanate Zirconate/Gold-Coated Glass Cantilevers at any Relative Humidity," *Sensors and Actuators* B, 125, 379-388 (2007).

Q. Zhu, W. Y. Shih, and W.-H. Shih, "Length and Thickness Dependence of Longitudinal Flexural Resonance Frequency Shifts of a Piezoelectric Microcantilever Sensor due to Young's Modulus Change," *J. Appl. Phys.* 104, 074503 (2008).

(56) References Cited

OTHER PUBLICATIONS

Q. Zhu, W. Y. Shih, and W.-H. Shih, "Enhanced Detection Resonance Frequency Shift of a Piezoelectric Microcantilever Sensor by a DC Bias Electric Field in Humidity Detection," Sensors and Actuators, B 138, 1 (2009).

Q. Zhu, W. Y. Shih, and W.-H. Shih, "Mechanism of the Flexural Resonance Frequency Shift of a Piezoelectric Microcantilever Sensor in a DC Bias Electric Field," Appl. Phys. Lett. 92, 033503 (2008).

Shin, S., Kim, J.P., Sim, S.J. & Lee, J. A multisized piezoelectric microcantilever biosensor array for the quantitative analysis of mass and surface stress. Applied Physics Letters 93,—(2008).

Pang, W. et al. Femtogram mass sensing platform based on lateral extensional mode piezoelectric resonator. Applied Physics Letters 88,—(2006).

Cherian, S. & Thundat, T. Determination of adsorption-induced variation in the spring constant of a microcantilever. Applied Physics Letters 80, 2219-2221 (2002).

Lee, J.H., Kim, T.S. & Yoon, K.H. Effect of mass and stress on resonant frequency shift of functionalized $Pb(Zr_{0.52}Ti_{0.48})O_3$ thin film microcantilever for the detection of C-reactive protein. Applied Physics Letters 84, 3187-3189 (2004).

Lee, J.H. et al. Immunoassay of prostate-specific antigen (PSA) using resonant frequency shift of piezoelectric nanomechanical microcantilever. Biosensors and Bioelectronics 20, 2157-2162 (2005).

Shen, Z., Shih, W.Y. & Shih, W.-H. Self-exciting, self-sensing $Pb Zr_{0.53}Ti_{0.47}O_3/SiO_2$ piezoelectric microcantilevers with femtogram/Hertz sensitivity. Applied Physics Letters 89, 023506-3 (2006).

Zhu, Q., Shih, W.Y. & Shih, W.-H. In situ, in-liquid, all-electrical detection of Salmonella typhimurium using lead titanate zirconate/gold-coated glass cantilevers at any dipping depth. Biosensors and Bioelectronics 22, 3132-3138 (2007).

McGovern, J.P. et al. Label-free flow-enhanced specific detection of Bacillus anthracis using a piezoelectric microcantilever sensor. Analyst 133, 649-654 (2008).

McGovern, J.P., Shih, W.Y. & Shih, W.H. In situ detection of Bacillus anthracis spores using fully submersible, self-exciting, self-sensing PMN-PT/Sn piezoelectric microcantilevers. Analyst 132, 777-783 (2007).

McGovern, J.-P. et al. Label-free flow-enhanced specific detection of Bacillus anthracis using a piezoelectric microcantilever sensor. The Analyst 133, 649-654 (2008).

McGovern, J.-P., Shih, W.Y. & Shih, W.-H. In situ detection of Bacillus anthracis spores using fully submersible, self-exciting, self-sensing PMN-PT/Sn piezoelectric microcantilevers. The Analyst 132, 777-783 (2007).

Zhu, Q., Shih, W.Y. & Shih, W.-H. Mechanism of flexural resonance frequency shift of a piezoelectric microcantilever sensor during humidity detection. Applied Physics Letters 92, 183505-3 (2008).

Su, W.-S., Chen, Y.-F., Shih, W.Y., Luo, H. & Shih, W.-H. Domain switching in lead magnesium niobate-lead titanate polycrystalline sheets at single grain level. Applied Physics Letters 91, 112903-3 (2007).

Shang, J.K. & Tan, X. Indentation-induced domain switching in Pb(Mg1/3Nb2/3)O3—PbTiO3 crystal. Acta Materialia 49, 2993-2999 (2001).

Alguero, M., Jimenez, B. & Pardo, L. Rayleigh type behavior of the Young's modulus of unpoled ferroelectric ceramics and its dependence on temperature. Applied Physics Letters 83, 2641-2643 (2003).

Masys, A.J., Ren, W., Yang, G. & Mukherjee, B.K. Piezoelectric strain in lead zirconate titante ceramics as a function of electric field, frequency, and dc bias. Journal of Applied Physics 94, 1155-1162 (2003).

Capobianco, J.A., Shih, W.Y., Yuan, Q.-A., Adams, G.P. & Shih, W.-H. Label-free, all-electrical, in situ human epidermal growth receptor 2 detection. Review of Scientific Instruments 79, 076101 (2008).

Shih, W.Y., Luo, H., Li, H., Martorano, C. & Shih, W.-H. Sheet geometry enhanced giant piezoelectric coefficients. Applied Physics Letters 89, 242913-3 (2006).

Capobianco, J.A., Shih, W.Y. & Shih, W.-H. 3-mercaptopropyltrimethoxysilane as insulating coating and surface for protein immobilization for piezoelectric microcantilever sensors. Review of Scientific Instruments 78, 046106 (2007).

Morton, T.A., Myszka, D.G. & Chaiken, I.M. Interpreting Complex Binding-Kinetics from Optical Biosensors—a Comparison of Analysis by Linearization, the Integrated Rate-Equation, and Numerical-Integration. Analytical Biochemistry 227, 176-185 (1995).

Shuck, P. & Minton, A.P. Kinetic analysis of biosensor data: elementary test of self-consistency. Trends Biochemical Sciences 21, 458-460 (1996).

McKendry, R. et al. Multiple label-free biodetection and quantitative DNA-binding assays on a nanomechanical cantilever array. Proceedings of the National Academy of Sciences of the United States of America 99, 9783-9788 (2002).

Ndieyira, J.W. et al. Nanomechanical detection of antibiotic mucopeptide binding in a model for superbug drug resistance. Nature Nanotechnology 3, 691-696 (2008).

Sofian M. Kanan and Carl P. Tripp, "An Infrared Study of Adsorbed Organophosphonates on Silica: A Prefiltering Strategy for the Detection of Nerve Agents on Metal Oxide Sensors," Langmuir 2001, 17, 2213-2218, United States of America.

"Enhanced detection resonance frequency shift of a piezoelectric microcantilver sensor by a DC bias electric field in humidity detection," Sensors and Actuators B: Chemical, 2009, vol. 138, United States of America.

J. K. Shang and X. Tan, "Indentation-Induced Domain Switching in Pb(Mg1/3Nb2/3)03—PbTiO3 Crystal" Acta Mater., 2001, pp. 2993-2999, vol. 49, Urbana, Illinois.

IEEE Standard on Piezoelectricity IEEE, New York, 1988, Chap. 6.

L. Bellaiche and David Vanderbilt, Physical Review Letters, 83(7), Aug. 16, 1999, 1347.

S-F. Liu, W. Ren, B. K. Mukherjee, S. J. Zhang, T. R. Shrout, P. W. Rehrig, and W. S. Hackenberger, Appl. Phys. Lett., 83, 2886 (2003).

PZT data, IEEE Micro Electro Mechanical Systems Workshop, Jan.-Feb. 1991, Nara, Japan p. 118.

Xu, et al., "Longtitudinal piezoelectric coefficient measurement for bulk ceramics and thin films using pneumatic pressure rig," Journal of Applied Physics, Jul. 1, 1999, pp. 588-594, vol. 86, No. 1, Pennsylvania.

Li, "Sodium Potassium Niobate-based Lead-free Piezoelectric Ceramics: Bulk and Freestanding Thick Films," Thesis Submitted to Faculty of Drexel University, Jun. 2008, Philadelphia, Pennsylvania.

Li, "Synthesis of Na0.5K0.5NbO3 Piezoelectrics by a Solution Coating Approach," Int. J. Appl. Technol., 2009, pp. 205-215, vol. 6, Issue 2, United States of America.

Hudson, J.B. Surface Science: An Introduction, (Wiley-IEEE, New York, 1998).

Q. Zhu. "Enhanced detection resonance frequency shift of a piezoelectric microcantilever sensor by a DC bias electric field in humidity detection," Sensors and Actuators B: Chemical, 2009, pp. 1-4, vol. 138.

Q. Zhu, W. Y. Shih & W.H. Shih, "mechanism of flexural resonance frequency shift of a piezoelectric microcantilever sensor during humidity detection," Applied Physics Letters, 2008, vol. 92, United States of America.

Hudson, J.B. Surface Science: An Introduction, Wiley-IEEE, 1998, pp. 96-98, New York.

Leckband, D.E. et al. Force Probe Measurements of Antibody-Antigen Interactions. Methods 20, 329-340 (2000).

O'Sullivan, C.K. & Guilbault, G.G. Commercial quartz crystal microbalances—theory and applications. Biosensors & Bioelectronics 14, 663-670 (1999).

Lofgren, J.A. et al. Comparing ELISA and surface plasmon resonance for assessing clinical immunogenicity of panitumumab. J Immunol 178, 7467-72 (2007).

Borghaei, et al., "induction of Adaptive Anti-HER2/neu Immune Responses . . . " J. Immunother, Jun. 2007, pp. 455, vol. 30, No. 4.

H. Yengingil, "Breast Cancer Detection and Differentiation Using Piezoelectric Fingers," PhD Thesis, Drexel University, Philadelphia, PA, Jan. 2009.

(56) References Cited

OTHER PUBLICATIONS

E. E. Konofagou, T. Harrigan, and J. Ophir, "Shear Strain Estimation and Lesion Mobility Assessment in Elastography," Ultrasonics, 2000, pp. 400-404, vol. 38.

H.O. Yegingil, W. Y. Shih, W. Anjum, A. D. Brooks and W.-H. Shih, "Soft tissue elastic modulus measurement and tumor detection using piezoelectric fingers," Mat. Res. Soc. Symp. Proc., 2006, vol. 898E.

P. S. Wellman, E. P. Dalton,, D. Krag,, K. A. Kern, R. D. Howe, "Tactile Imaging of Breast Masses: First Clinical Report," Archives of Surgery 136(2), 204-08 (2001).

Z. Shen, W. Y. Shih, and W. -H. Shih, "Mass detection sensitivity of piezoelectric cantilevers with a nonpiezoelectric extension," Rev. Sci. Instrum. 77, 065101 (2006).

A. Markidou, W. Y. Shih, and W.-H. Shih, "Soft-materials elastic and sear moduli measurement using piezoelectric cantilevers," Rev. Sci. Ins. 76, 064302 (2005).

S . T. Szewczyk, W.Y. Shih, and W.-H. Shih, "Palpationlike soft-material elastic modulus measurement using piezoelectric cantilievers," Rev. Sci. Ins., 77, 044302 (2006).

H. O. Yegingil, W. Y. Shih, and W.-H. Shih, "All-electrical indentation shear modulus and elastic modulus measurement using a piezoelectric cantilever with a tip," J. Appl. Phys., 101, 054510 (2007).

W. Jiang and W. Cao, "Intrinsic and coupling-induced elastic nonlinearity of lanthanum-doped lead magnesium niobate-lead titanate electrostrictive ceramic," Appl. Phys. Lett., 77,1387 (2000).

A. W. McFarland, et al., "Influence of surface stress on the resonance behavior of microcantilevers," Appl. Phys. Lett. 87, 053505 (2005).

O. Kwon, "T-scan Electrical Impedance Imaging system for anomaly detection," Siam J. Appl. Math., 2004, pp. 252-266, vol. 65, No. 1.

Sure Touch Exam [online] retrieved Nov. 29, 2010 from the internet @ http://www.medicaltactile.com/default.htm.

Q. Ren and Y. P. Zhao, "Influence of surface stress on frequency of microcantilever-based biosensors," Microsystem Technologies, 2004, pp. 307-314, vol. 10.

E. Chen, "Ultrasound Tissue Displacement and Tissue Elasticity Imaging," Ph.D. dissertation, University of Illinois at Urbana-Champaign, (1995).

Haun, M.J. "Thermodynamic Theory of the Lead Zirconate-Titanate Solid Solution System," The Pennsylvania State University (1988).

Lee, C. et al., "Sol-gel derived PZT force sensor for scanning force microscopy", Mater. Chem. Phys., 44: 25-29 (1996).

Lee, C. et al., "Self-excited piezoelectric PZT microcantilevers for dynamic SFM—with inherent sensing and actuating capabilities", Sensors and Actuators, A72: 179-188 (1999).

Lee, J. H. et al., "Label free novel electrical detection using micromachined PZT monolithic thin film cantilever for the detection of C-reactive protein", Biosensors and Bioelectronics, 20: 269-275 (2004).

Lee, J. H. et al., "Effect of mass and stress on resonant frequency shift of functionalized Pb(Zr0.52Ti0.48)O3 thin film microcantilever for the detection of C-reactive protein", Appl. Phys. Lett., 84(16): 3187-3189 (2004).

Lee, J. H. et al., "Immunnoassay of prostate-specific antigen (PSA) using resonant frequency shift of piezoelectric nanomechanical microcantilever", Biosensors and Bioelectronics, 20: 2157-2162 (2005).

Lee, S. S. et al., "Self-Excited Piezoelectric Cantilever Oscillators", The 8th International Conference on Solid-State Sensors and Actuators, and Eurosensors IX, Stockholm, Sweden: 417-420 (1995).

Lee, Y. et al., "A Piezoelectric Micro-Cantilever Bio-Sensor Using the Mass-Microbalancing Technique With Self-Excitation", The 13th International Conference on Solid-State Sensors, Actuators, and Microsystems, Seoul, Korea: 644-647 (2005).

Li, S. et al., "The intrinsic nature of nonlinear behavior observed in lead zirconate titanate ferroelectric ceramic", J. Appl. Phys., 69(10): 7219-7224 (1991).

Li, Z. et al., "Detection of water-ice transition using a lead zirconate titanate/brass transducer", J. Appl. Phys., 92(1): 106-111 (2002).

Lin, Z. et al., "Operation of an Ultrasensitive 30-MHz Quartz Crystal Microbalance in Liquids", Anal. Chem., 65(11): 1546-1551 (1993).

Liu, W. et al., "Preparation and orientation control of Pb1.1(Zr0.3Ti0.7)O3 thin films by a modified sol-gel process", Mat. Lett., 46: 239-243 (2000).

Luo, H. et al., "Comparison in the Coating of Mg(OH)2 on Micron-Sized and Nanometer-Sized Nb2O5 Particles", Int. J. Appl. Ceram. Technol., 1(2): 146-154 (2004).

Luo, H., "Colloidal Processing of PMN-PT Thick Films for Piezoelectric Sensor Applications", A Thesis Submitted to the Faculty of Drexel University in Jun. of 2005.

Maki, K. et al., "Evaluation of Pb(Kr,Ti)O3 Films Derived from Propylene-Glycol-Based Sol-Gel Solutions", Jpn. J. Appl. Phys., 39(9B): 5421-5425 (2000).

Matsui, Y. et al., "Highly Oxidation-Resistant TiN Barrier Layers for Ferroelectric Capacitors", Jpn. J. Appl. Phys., 36 (3B): 1586-1588 (1997).

McGovern, J.P. et al., "Real-Time *Salmonella* Detection Using Lead Zirconate Titanate-Titanium Microcantilevers", Mater. Res. Soc. Symp. Proc., 845: AA3.8.1-AA3.8.6 (2005).

Mueller, V. et al., "Nonlinearity and scaling behavior in donor-doped lead zirconate titanate piezoceramic", Appl. Phys. Lett., 72(21): 2692-2694 (1998).

Mulvihill, M. L. et al., "The Role of Processing Variables in the Flux Growth of Lead Zinc Niobate-Lead Titanate Relaxor Ferroelectric Single Crystals", Jpn. J. Appl. Phys., 35(7): 3984-3990 (1996).

Niedziolka, J. et al., "Charaterisation of gold electrodes modified with methyltrimethoxysilane and (3-mercaptopropyl)trimethoxysilane sol-gel processed films", J. Electroanalytical Chem., 578: 239-245 (2005).

Nguyen, L. T. T. et al., "Synthesis and characterization of a photosensitive polyimide precursor and its photocuring behavior for lithography applications", Optical Materials, 29: 610-618 (2007).

Oden, P. I. et al., "Viscous drag measurements utilizing microfabricated cantilevers", Appl. Phys. Lett., 68(26): 3814-3816 (1996).

Ohnmacht, M. et al., "Microcoils and microrelays—an optimized multilayerfabrication process", Sensors and Actuators, 83: 124-129 (2000).

Park, G.T. et al., "Measurement of piezoelectric coefficients of lead zirconate titanate thin films by strain-monitoring pneumatic loading method", Appl. Phys. Lett., 80(24): 4606-4608 (2002).

Park, S.E. et al., "Ultrahigh strain and piezoelectric behavior in relaxor based ferroelectric single crystals", J. Appl. Phys., 82(4): 1804-1811 (1997).

Piezo Systems, Inc., "Piezoceraminc Sheets and Their Properties", Piezo Systems, Inc. Catalog: 1-3 (2007).

Pons, T. et al., "Solution-phase single quantum dot fluorescence resonance energy transfer", J. Amer. Chem. Soc., 128(47): 15324-15331 (2006). Abstract Only.

Ren, W. et al., "Non linear strain and DC bias induced piezoelectric behaviour of electrostrictive lead magnesium niobate-lead titanate ceramics under high electric fields", J. Phys. D: Appl. Phys., 35: 1550-1554 (2002).

Ren, W. et al., "Nonlinear behavior of piezoelectric lead zinc niobate-lead titanate single crystals under ac electric fields and dc bias", Appl. Phys. Lett., 83(25): 5268-5270 (2003).

Rosenberg, RD et al., "Effects of age, breast density, ethnicity and estrogen replacement therapy on screening mammographic sensitivity and cancer stage at diagnosis: review of 183,134 screening mammograms in Albuquerque, New Mexico", Radiology, 209(2): 511-5118 (1998). Abstract Only.

Saito, Y. et al., "Lead-free piezoceramics", Nature, 432: 84-87 (2004).

Schemmel, A. et al., "Single molecule force spectrometer with magnetic force control and inductive detection", Rev. Sci. Instrum., 70(2): 1313-1317 (1999).

Shen, Z. et al., "Microfabrication of Miniaturized PZT/SiO2 Piezoelectric Microcantilever for Rapid, Direct, In-situ Biosensing", MRS Fall Meeting, Boston: 1-23 (2005).

Shen, Z. et al., "Self-exciting, self-sensing PbZr0.53Ti0.47O3/SiO2 piezoelectric microcantilevers with femtogram/Hertz sensitivity", Appl. Phys. Lett., 89: 023506-1-023506-3 (2006).

(56) References Cited

OTHER PUBLICATIONS

Shih, W. et al., "Simultaneous liquid viscosity and density determination with piezoelectric unimorph cantilevers", J. Appl. Phys., 89(2): 1497-1505 (2001).

Shih, W. et al., "Ultrasensitive Pathogen Quantification in Drinking Water Using Highly Piezoelectric Microcantilevers", Amer. Chem. Soc., Chapter 23, 179-185 (2005).

Shih, W. et al., "Nanosensors for Environmental Applications", Nanotechnologies for the Life Sciences, 5: 271-293 (2005).

Straub, V. et al., "Contrast Agent-Enhanced Magnetic Resonance Imaging of Skeletal Musde Damage in Animal Models of Muscular Dystrophy", Magn. Reson. Med., 44: 655-659 (2000).

Thompson, W. R. et al., "Hydrolysis and Condensation of Self-Assembled Monolayers of (3-Mercaptopropyl) trimethoxysilane on Ag and Au Surfaces", Langmuir, 13: 2291-2302 (1997).

Thundat, T. et al., "Detection of mercury vapor using resonating microcantilevers", Appl. Phys. Lett., 66(13): 1695-1697 (1995).

Tslonsky, M. et al., "Sol-Gel-Derived Ceramic-Carbon Composite Electrodes: Introduction and Scope of Applications", Anal. Chem., 66: 1747-1753 (1994).

Tu, Y. L. et al., "A study of the effects of process variables on the properties of PZT films produced by a single-layer sol-gel technique", J. Mater. Sci., 30: 2507-2516 (1995).

Udayakumar, K. R. et al., "Thickness-dependent electrical characteristics of lead zirconate titanate thin films", J. Appl. Phys., 77(8): 3981-3986 (1995).

Wang, Q.M. et al., "Nonlinear piezoelectric behavior of ceramic bending mode actuators under strong electric fields", J. Appl. Phys., 86(6): 3352-3360 (1999).

Ward, M. D. et al., "In Situ Interfacial Mass Detection with Piezoelectric Transducers", Science, 249: 1000-1007 (1990).

Wellman, P. S. et al., "Tactile Imaging of Breast Masses", Arch. Surg., 136: 204-208 (2001).

Weng, L. et al., "Effect of acetylacetone on the preparation of PZT materials in sol/gel processing", Mater. Sci. Engin., B96: 307-312 (2002).

Wilson, L S et al., "Elastography—the movement begins", Phys. Med. Biol., 45: 1409-1421 (2000).

Wilson, L., et al., "Pezoelectric-excited millimeter-sized cantilever (PEMC) sensor provides viscosity and density measurements," Submitted to Review of Scientific Instruments, 1-26, (2007).

Yi, J. W. et al., "Effect of length, width, and mode on the mass detection sensitivity of piezoelectric unimorph cantilevers", J. Appl. Phys., 91(3): 1680-1686 (2002).

Yi, J. W. et al., "In situ cell detection using piezoelectric lead zirconate titanate-stainless steel cantilevers", J. Appl. Phys., 93(1): 619-625 (2003).

Zhao, Q. et al., "Array adsorbent-coated lead zirconate titanate (PZT)/stainless steel cantilevers for dimethyl methylphosphonate (DMMP) detection", Sensors and Actuators, B117(1): 74-79 (2006). Abstract Only.

Zhou, J. et al., "Zeolite-modified microcantilever gas sensor for indoor air quality control," Sensors and Actuators B, Oct. 1, 2003, 94(3), 337-342.

Zhu, D.M. et al., "Thermal conductivity and electromechanical property of single-crystal lead magnesium niobate titanate", Appl. Phys. Lett., 75(24): 3868-3870 (1999).

Data of Commercially Available Product, EDO Corporation: 1-8 (1999).

Data of Commercially Available Product, APC International, Ltd.: 1-2 (2005).

Campbell, G.A., et al., "Use of Piezoelectric-Excited millimeter Sized Cantilever Sensors to Measure Albumin Interaction with Self-Assembled Monolayers of Alkanethiols Having Different Functional Headgroups," Anal. Chem. 78, 2328-2334 (2006).

Campbell, G.A., et al., "Method of measuring Bacillus anthracis spores in the Presence of copious amounts of Bacillus thurigiensis and Bacillus cereus," Anal. Chem. 79, 1145-1152 (2007).
Campbell, G.A., et al., "PEMC sensor's mass change sensitivity is 20 pg/Hz under liquid immersion," Biosensors and Bioelectronics, 22, 35-41 (2006).
Campbell, G.A., et al., "Detection of *Bacillus anthracis* spores and a model protein usings PEMC sensors in a flow cell at 1 mL/min," Biosensors and Bioelectronics, 22, 78-85 (2006).
Campbell, G.A., et al., "Detection of airborne *Bacillus anthracis* spores by an integrated system of an air sampler and a cantilever immunosensor," Sensors and Actuators B 127, 376-382 (2007).
Maraldo, et al., "Method for Label-Free Detection of Femtogram Quantities of Biologics in Flowing Liquid Samples," Anal. Chem. 79, 2762-2770 (2007).
Maraldo, et al., "Detection and confirmation of staphylococcal enterotoxin B in apple juice and milk using piezoelectric-excited millimeter-sized cantilever sensors at 2.5 fg/mL," Anal Chem. 79, 7636-7643 (2007).
Maraldo, et al., "Method for Quantification of a Prostate Cancer Biomarker in Urine without Sample Preparation," Anal. Chem. 79, 7683-7690 (2007).
Maraldo, et al., "10-Minute assay for detecting *Escherichia coli* O157:H7 in ground beef samples using piezoelectric-excited millimeter-size cantilever sensors." Journal of Food Protection, vol. 70, No. 7, 1670-1677 (2007).
Maraldo, et al., "Preapration-Free Method for Detecting *Escherichia coli* O157:H7 in the Presence of Spinach, Spring Lettuce Mix, and Ground Beef Particulates," Journal of Food Protection, vol. 70, No. 11, 2651-2655 (2007).
Rijal, et al., "PEMC-based method of measuring DNA hybridization at femtomolar concentration directly in human serum and in the presence of copious noncomplementary strands," Anal. Chem., 79, 7392-7400 (2007).
Rijal, et al., "Method for measuring the Self-Assembly of Alkanethiols on Gold at Femtomolar Concentrations," Langmuir, 23, 6856-6863 (2007).
Wilson, et al., "Viscosity and density values from excitation level response of piezoelectric-excited cantilever sensors," Sensors and Actuators A 138, 44-51 (2007).
Gu, et al., "Single-Calcination Synthesis of Pyrochlore-Free 0.9Pb (Mg1/3Nb2/3)O3-0.1PbTiO3 and Pb(Mg1/3Nb2/3)O3 Ceramics using a Coating Method," J. Am. Ceram. Soc., 86 [2] 217-21 (2003).
Thaysen, et al., "Cantilever-Based Bio-Chemical Sensor Integrated in a Microliquid Handling System," 401-404 (2001).
Thaysen, "Label free Detection, BioMEMs Materials and Fabrication Methods," Track 2, 3:00pm, pp. 1-3, Sep. 7, 2002.
Rebecca Ferrini, MD, Elizabeth Mannino, MD, Edith Ramsdell, MD and Linda Hill, MD, MPH, *Screening Mammography for Breast Cancer: American College of Preventive Medicine Practice Policy Statement*, American Journal of Preventive Medicine Sep./Oct. 1996; 12(5):340-41, pp. 1-4.
Anne Keller, MD, Ragnhild Gunderson, MD, Olav Reikeras, MD, PhD and Jens I. Brox, MD, PhD, *Reliability of Computed Tomography Measurements of Paraspinal Muscle Cross-Sectional Area and Density in Patients with Chronic Low Back Pain*, SPINE vol. 28, No. 13, pp. 1455-1460, (2003).
Volker Straub, Kathleen M. Donahue, Valerie Allamand, Robin L. Davisson, Young R. Kim and Kevin P. Campbell, *Contrast Agent-Enhanced Magnetic Resonance Imaging of Skeletal Muscle Damage in Animal Models of Muscular Dystrophy*, Magnetic Resonance in Medicine 44:655-659 (2000).
Habib Ammaru, Ohin Kwon, Jim Keun Seo, and Eung Je Woo, *T-Scan Electrical Impedance Imaging System for Anomaly Detection*, Siam J., Appl. Math., vol. 65, No. 1, pp. 252-266 © 2004 Society for Industrial and Applied Mathematics.
Stephane G. Carlier, Chris L. de Korte, Elisabeth Brusseau, Johannes A. Schaar, Patrick E. Serruys and Anton F.W. van der Steen, *Elastography*, Journal of Cardiovascular Risk 2002, 9:237-245.
Rosenberg RD, Hunt WC, Williamson MR, Gilliland FD, Wiest PW, Kelsey CA, Key CR, Linver MN, *Effects of age, breast density, ethnicity, and estrogen replacement therapy on screening mammographic sensitivity and cancer stage at diagnosis: review of 183, 134 screening mammograms in Albuquerque, New Mexico*, Radiology, Nov. 1998; 209(2):511-8.

(56) References Cited

OTHER PUBLICATIONS

S A Kruse, J A Smith, A J Lawrence, M A Dresner, A Manduca, J F Greenleaf and R L Ehman, *Tissue characterization using magnetic resonance elastography: preliminary results*, Phys. Med. Biol. 45 (2000) 1579-1590.

L S Wilson, D E Robinson and M J Dadd, *Elastography—The Movement Begins*, Phys. Med. Biol. 45 (2000) 1409-1421.

Parris S. Wellman, PhD, Edward P. Dalton, MD, David Krag, MD, Kenneth A. Kern, MD, Robert D. Howe, PhD, *Tacticle Imaging of Breast Masse*, (Reprinted) Arch Surg/vol. 136, Feb. 2001.

James F. Greenleaf, Mostafa Fatemi, and Michael Insana, *Selected Methods for Imaging Elastic Properties of Biological Tissues*, Annu. Rev. Biomed. Eng. 2003 5:57-78.

\* cited by examiner

Figure 6(a)
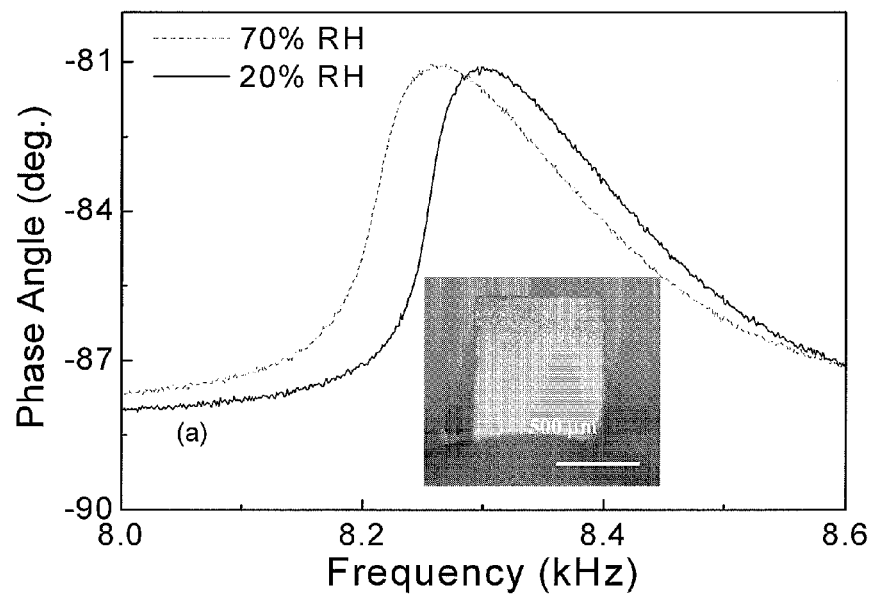
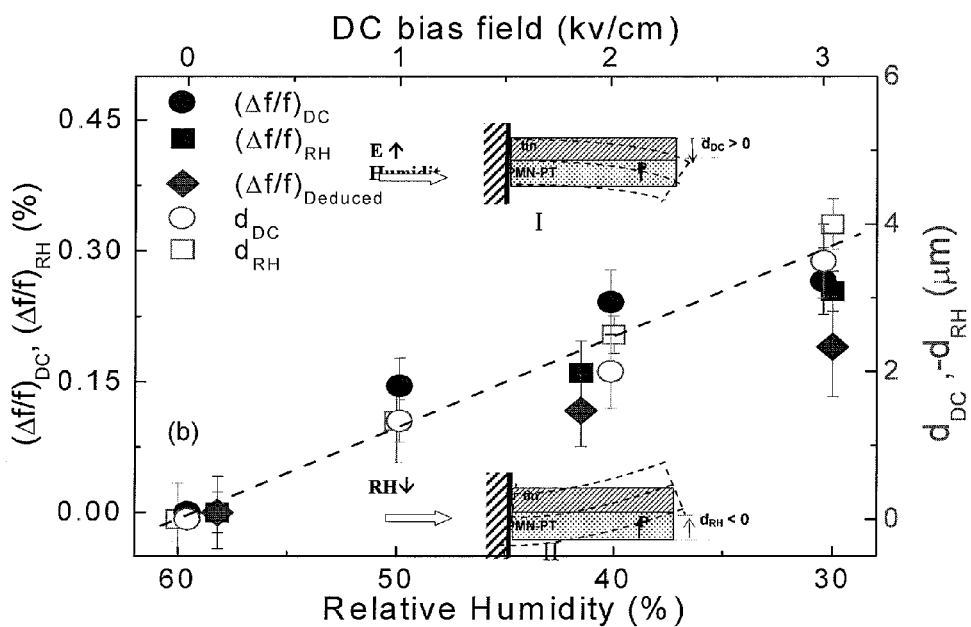
Figure 6(b)

ENHANCED DETECTION SENSITIVITY WITH PIEZOELECTRIC SENSORS

STATEMENT OF GOVERNMENT INTEREST

This invention was reduced to practice with Government support under Grant No. RO1 EB000720 awarded by the National Institutes of Health; the Government is therefore entitled to certain rights to this invention. Some research for this invention was supported by the Commonwealth of Pennsylvania's Ben Franklin Technology Development Authority through the Ben Franklin Technology Partners of Southeastern Pennsylvania as fiscal agents for the Nanotechnology Institute.

BACKGROUND OF THE INVENTION

1. Field of the Invention

The invention relates to methods and systems for enhancing the detection sensitivity of piezoelectric microcantilevers. The method of the present invention may be particularly beneficial for biodefense, food safety, pathogen detection and diagnostic applications involving body fluids such as serum, saliva, and urine.

2. Description of the Related Technology

Piezoelectric sensor technologies, specifically piezoelectric cantilever sensors, are useful for detecting the presence and/or mass of various compounds and molecules. Typically millimeter-sized, these cantilever sensors are fabricated by bonding a thick layer of a piezoelectric material, such as commercial lead zirconate titanate (PZT), to a non-piezoelectric substrate, such as stainless steel, titanium or glass, and have a number of advantageous properties, such as the capability of electrical self-excitation and self-sensing. Furthermore, piezoelectric cantilevers that include an insulation layer are capable of preventing conduction in liquid media, rendering them promising for biological in-situ electrical detection. Current piezoelectric cantilever sensors, however, generally lack the desired detection sensitivity necessary for many applications, particularly in-situ biosensing applications. These sensors typically have poor piezoelectric properties, characterized by a low $-d_{31}$ piezoelectric coefficient of less than 20 pm/v.

The detection sensitivity of piezoelectric cantilever sensors, which may be viewed as simple harmonic oscillators, is correlated to the resonance frequency shift capability of the sensor. The resonance frequency shift capability in turn is dependent upon the ability to detect changes in the effective spring constant and effective mass of the sensor. Current cantilever sensor technologies, such as non-piezoelectric microcantilevers and piezoelectric microcantilevers constructed from bulk PZT of relatively large thickness are only useful for methods which detect changes in mass and/or minor changes in the effective spring constant of the sensor.

Enhancement of detection sensitivity, accuracy and efficiency of piezoelectric cantilever sensors would be useful to the development of numerous industries and technological fields, such as bioterrorism defense, health sciences and diagnostic devices. Therefore, there is a need to develop a piezoelectric microcantilever sensor capable of achieving very high detection sensitivities.

SUMMARY OF THE INVENTION

In one aspect, the present invention is directed to methods for enhancing detection sensitivity of a piezoelectric microcantilever sensor. One such method involves providing a piezoelectric microcantilever sensor, applying a DC bias electric field to the sensor.

In another aspect, the method involves providing a piezoelectric microcantilever sensor wherein binding of the species of interest to the sensor induces a significant change in the Young's modulus of the piezoelectric layer.

In another aspect, the invention relates to a piezoelectric microcantilever sensor sensing system having enhanced detection sensitivity comprising a piezoelectric microcantilever sensor and a DC bias electric field generation means.

BRIEF DESCRIPTION OF THE DRAWINGS

FIG. 6(a) is a graph of flexural-mode resonance spectra at 20% and 70% relative humidity. The insert figure is a top view of an optical micrograph of the PEMS.

FIG. 6(b) is a graph of $(\Delta f/f)_{RH}$ and $-d_{RH}$ as a function of relative humidity and $(\Delta f/f)_{DC}$ and $d_{DC}$ as a function of E of the PEMS. The insert figures show bending of the PEMS with an increasing E and a decreasing relative humidity, respectively.

DETAILED DESCRIPTION OF THE PREFERRED EMBODIMENTS

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

It must be noted that as used herein and in the appended claims, the singular forms "a", "an", and "the" include plural references unless the context clearly dictates otherwise. Thus, for example, reference to "a sensor" includes a plurality of sensors and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

For purposes of the present invention, the terms "width mode", "length mode" and "thickness mode" refer to various modes of use of the sensors for detection. Specifically, these modes refer to the direction of the induced stress relative to the cantilever sensor.

Additionally, for the purpose of this patent application, Q value is defined as the ratio of the resonance frequency to the resonance peak width at half the peak height.

The present invention pertains to various methods and systems for enhancing the detection sensitivity of cantilever sensors, particularly piezoelectric microcantilever sensors (PEMS) which use an electrical means for detection. Specifically, the method of the present invention involves providing a PEMS and using the PEMS to detect the presence or mass of a species of interest. It has been found that for certain PEMS sensors, a change in the Young's modulus of at least one piezoelectric layer of the PEMS sensor can be induced by the species of interest, thereby significantly enhancing the detection sensitivity of the sensor. The method of the present invention enables a PEMS to quickly, accurately and efficiently determine the presence and/or mass of a species of interest with a high level of detection sensitivity.

Figure 1:
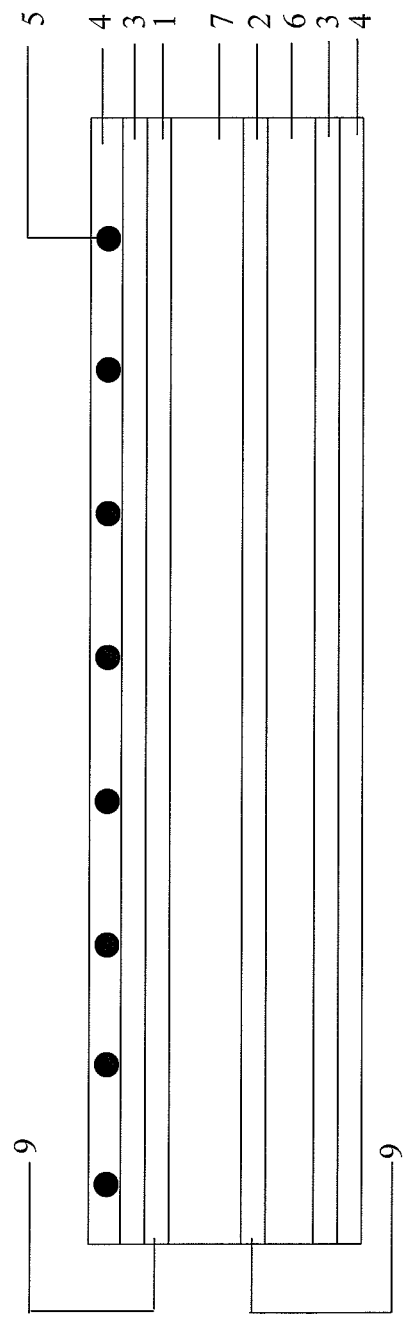
FIG. 1 is a cross-sectional view of one embodiment of a piezoelectric microcantilever in accordance with the present invention.

FIG. 1 shows the basic structure of a PEMS. The PEMS may include a first conductive element 1 and a second conductive element 2 (bottom electrode), a piezoelectric layer 7 located between the conductive elements 1, 2, receptors 5 located on said piezoelectric layer 7 and an optional receptor immobilization layer 4. For applications involving detection in, for example, liquid media, the PEMS may further include an electrically insulating layer 3 in order to increase tolerance of liquid damping or other environmental dampening.

In general, the effective mass and/or the effective spring constant of the piezoelectric layer change as a result of binding of a target species to the PEMS. By monitoring resonance frequency shifts which result from the mass and/or spring constant changes, the PEMS is capable of rapid, label-free, quantitative detection of various species, including pathogens, antigens, proteins, and DNA in a small volume of a sample medium (e.g. 100 μl) or in a cell culture using simple all-electrical measurements. The PEMS is capable of electric actuation and detection and may be used to create a PEMS array to enable simultaneous monitoring of multiple target compounds or molecules.

Conductive elements 1, 2 may be any element capable of conducting an electrical signal from the piezoelectric layer to a device for detecting that signal. In a preferred embodiment, conductive elements 1 and 2 are electrodes which may be constructed from any conductive material. Preferably, the first electrode 1 is constructed from Au/Cr or Pt/Ti and subsequently patterned in several regions. The second electrode 2 is preferably constructed from Pt/TiO$_2$ on SiO$_2$ for PZT/SiO$_2$ PEMS or Pt/Ti or Au/Cr on a metal substrate or non-piezoelectric layer. The electrode may be subsequently patterned.

Receptors 5 may be densely packed and immobilized onto, for example, any bi-functional linker modified sensor surface. Any receptor, such as specially synthesized cavitants, DNA oligonucleotides, proteins, single chain variable fragments (scFvs), enzymes, and antibodies to cells, antigens or pathogens, may be bound to any surface of the sensor. In an exemplary embodiment, receptors 5 cover as much of the sensor surface as possible. Preferably, receptors 5 cover the major faces of piezoelectric layer 7 and an optional non-piezoelectric layer 6. For example, when trying to detect cancer, monomeric and dimeric anti-tumor scFv molecules, which are composed of variable light and heavy chains of antibody molecule anti-ECD scFV that react to cancer markers, may be employed. Similarly, when trying to detect *Bacillus anthracia* ("BA"), antibodies specific to BA spore surface antigens may be employed.

Any means of adhering receptors 5 to a sensor surface may be utilized. In a preferred embodiment, receptors 5 may be bound to a surface of the sensor using an immobilization layer 4, such as self assembled monolayers ("SAM"), mercaptopropylsilane (MPS) and bi-functional linkers. In one exemplary embodiment, for purposes of binding scFv, the immobilization coating may be a self assembled monolayer of 3-mercaptoproprionic acid (MPA) on a copper, platinum, or gold-coated electrode activated with 1-ethyl-3-(3-dimethylaminopropy)carbodimide hydrochloride (EDC) and 5 mg/ml N-hydroxysulfosuccinimide (NHS).

In one embodiment, the piezoelectric microcantilever includes a highly piezoelectric layer 7, which enables electrical detection and actuation within the cantilever. The piezoelectric layer may function as a driving element, vibrating element, sensing element, or a combination thereof. Preferably, piezoelectric layer 7 is a driving, vibrating and sensing element. Applying an AC voltage (input) across piezoelectric layer 7 bends and vibrates the PEMS, which in turn induces a piezoelectric voltage that produces readily detectable changes in the magnitude and phase of the output voltage. The resonance frequency of the PEMS may be obtained, for example, by monitoring the maximum of the phase shift of the output voltage. This measurement is accomplished all-electrically, i.e., electrical actuation and electrical sensing.

Piezoelectric layer 7 may be constructed from any piezoelectric material, preferably highly piezoelectric materials, such as lead magnesium niobate-lead titanate $(Pb(Mg_{1/3}Nb_{2/3})O_3)_{1-x}$—$(PbTiO_3)_x$ $(PMN_{1-x}$-$PT_x)$ films (PMN-PT), where $0.3<x<0.4$, highly piezoelectric lead zirconate titanate (PZT) films and sodium potassium niobate-lithium niobate solid solutions (NKN-LN). In an exemplary embodiment, piezoelectric layer 7 may be fabricated from any highly piezoelectric material with a high $-d_{31}$ coefficient of about 20 pm/V$<-d_{31}<$5000 pm/V, preferably about 200 pm/V$<-d_{31}<$5000 pm/V, more preferably, about 500 pm/V$<-d_{31}<$5000 pm/V and most preferably, about 2000 pm/V$<-d_{31}<$5000 pm/V. In another exemplary embodiment, the $-d_{31}$ coefficient may be greater than about $20\times10^{-12}$ mN. Additionally, piezoelectric layer 7 may have a piezoelectric coefficient $d_{33}$ greater than about $40\times10^{-12}$ m/V.

Piezoelectric layer 7 may have any structural configuration or dimension. In one exemplary embodiment, piezoelectric layer 7 may be rectangular, triangular, circular, elliptical, or any other geometric shape. In another exemplary embodiment, the piezoelectric layer has a thicknesses of about 0.5 µm to about 250 µm, more preferably about 0.5 µm to about 127 µm and most preferably about 0.5 µm to about 100 µm. Piezoelectric layer 7 may further have a length of about 1 µm to about 3 mm and a width of about 1 µm to about 3 mm. In yet another exemplary embodiment, piezoelectric layer 7 may further have a length of about 10 µm to about 3 mm and a width of about 0.5 µm to about 3 mm.

Optionally, the PEMS may also include at least one non-piezoelectric layer 6, which may be fabricated from any compatible material, including ceramic, polymeric, plastic, metallic material or a combination thereof. In an exemplary embodiment, non-piezoelectric layer 6 may be fabricated from silicon dioxide ($SiO_2$) or silicon nitride ($Si_3N_4$) for PZT-thin film based PEMS. In another exemplary embodiment, non-piezoelectric layer 6 may be fabricated from a metal such as Cu, Sn, Ni, Ti, or any combination thereof. Non-piezoelectric layer 6 may also have any structural configuration or dimension. In one exemplary embodiment, non-piezoelectric layer 6 may be rectangular, triangular, circular, elliptical, or any other geometric shape. In another exemplary embodiment, non-piezoelectric layer 6 may have a length of 1 µm to about 3 mm, a width of about 1 µm to about 3 mm and a thickness of about 0.05 µm to about 100 µm.

The piezoelectric microcantilever of the present invention includes a piezoelectric layer 7. In another exemplary embodiment, the PEMS may include a piezoelectric layer 7 and optionally, at least one non-piezoelectric layer 6. Piezoelectric layer 7 and/or optional non-piezoelectric layer 6 may be attached to a clamp. The microcantilever may have a wide variety of structural configurations. In one exemplary embodiment, a piezoelectric layer 7 may be bonded to a non-piezoelectric layer 6 that is shorter, longer or equal in length. Preferably, non-piezoelectric layer 6 may be shorter than or extend beyond piezoelectric layer 7, so as to form a cantilever tip. When flexural modes are not used, the preferred PEMS need not have a non-piezoelectric layer 6 so as to maximize the length-mode or width-mode resonance frequency shift. In yet another exemplary embodiment, a piezoelectric layer 7 may be wider than, narrower than or equal in one or more dimensions with respect to non-piezoelectric layer 6.

For applications involving detection in a liquid, the PEMS may further include an electrically insulating layer 3 in order to electrically separate or buffer conductive element 1 and second conductive element 2, thereby maintaining functionality by preventing conduction. Conductive element 1 may be patterned slightly smaller than the piezoelectric layer 7 to ensure complete insulation of the edges and corners thereof. Any electrically insulating layer 3 may be used as a coating to achieve electrical separation or buffering.

In one embodiment, insulating layer 3 may comprise a 1.5 µm thick parylene (poly-para-xylylene) coating deposited on a conductive element 1, 2 by chemical vapor deposition. When placed in static and 1 ml/min flow rate of PBS solution, a parylene insulating layer 3 essentially prevents background resonance frequency shifts greater than 30 Hz and 60 Hz, respectively, over a period of 30 minutes. As a result, insulating layer 3 enables complete submersion of the microcantilever for in situ or in-liquid detection while maintaining a Q value (quality value) greater than about 35.

Alternatively, a PEMS may be insulated using self-assembled monolayers with hydrophobic properties, preferably methyltrimethoxysilane (MTMS) or a combination of MTMS with parylene coatings of varying thicknesses, may also be used. When immersed in a PBS solution, an MTMS insulated piezoelectric microcantilever yields strong resonance peak intensities and prevents background resonance frequency shifts greater than about 30 Hz over a period of 30 minutes.

Other insulation materials may include $Al_2O_3$, $SiO_2$ and any functional hydrophobic silane, having a hydrophobic group selected from the group consisting of alkyl, phenyl, alkyl halide, alkene, alkyne, and sulfhydryl. In an exemplary embodiment, the insulation material is mercaptopropylsilane (MPTS), which can also function to immobilize a receptor on the cantilever.

The resultant PEMS may be chemically inert, thermally stable and preferably miniaturized to enhance sensitivity. In an exemplary embodiment, the PEMS has a high detection sensitivity of about $1\times10^{-11}$ g/Hz or better, more preferably $1\times10^{-16}$ g/Hz or better and most preferably $1\times10^{-17}$ g/Hz or better. Preferably, the PEMS has a detection sensitivity of about $1\times10^{-19}$ g/Hz or better. Preferably, the PEMS may be electrically insulated to enable detection in any sample medium, including air, liquid or solid.

In operation, an alternating voltage may be applied to conductive element 1 to drive piezoelectric layer 7 of the self-actuating PEMS and a conductive element 2 may be used to detect a shift in the mechanical resonance frequency of the PEMS due to the binding of a target molecule or compound by the receptors. During this process, the method of the present invention involves inducing a positive or negative change in the Young's modulus of the piezoelectric layer, which is preferably a substantial change in the Young's modulus of the piezoelectric layer. In one exemplary embodiment, the change in the Young's modulus may be up to about 70%. The change in the Young's modulus of the piezoelectric layer is preferably greater than about 25%. Most preferably, the change in the Young's modulus may be about 25% to about 70%. One of the factors that induces a change in the Young's modulus is non-180° polarization domain switching.

By inducing and/or enhancing non-180° polarization domain switching, it may be possible to further increase the detection sensitivity of the PEMS in comparison to non-piezoelectric or weak piezoelectric microcantilevers of the same dimension. One means for inducing non-180° polarization domain switching may be application of stress produced by the binding of target molecules or compounds. In another exemplary embodiment, non-180° polarization domain switching may be induced by exposing the PEMS to a DC bias electric field. The DC bias electric field may be established using any conventional means and may involve applying a DC voltage across a thickness, length or width of piezoelectric layer 7. Preferably, the established DC bias electric field (E) is from about −20 kV/cm to about 20 kV/cm, more preferably, from about −10 kV/cm to about 10 kV/cm, and, most preferably, from about −8 kV/cm to about 10 kV/cm. A positive value for E denotes an applied electric field that is parallel to the poling direction of the piezoelectric layer. A negative value for E denotes an applied electric field that is opposite to the poling direction of the piezoelectric layer. By establishing a DC bias electric field, the flexural frequency shift and hence, detection sensitivity, may be further increased by a factor of up to about three in comparison to the sensitivity PEMS operated without a DC bias electric field. The DC bias electric field changes the polarization configuration such that it increases polarization domain switching, which in turn enhances the resonance frequency shift enabling enhanced detection sensitivity. The degree of detection sensitivity enhancement is dependent upon the piezoelectric material, the thickness of the piezoelectric layer, whether it is bonded to a non-piezoelectric layer, the physical properties, i.e. thickness and/or material characteristics of the non-piezoelectric layer and any combination thereof.

The method may further involve enabling detection of a species of interest using any resonance frequency peak and any resonance frequency modes. In an exemplary embodiment, the PEMS may be operated in a flexural resonance mode, a longitudinal resonance mode, such as a length mode, a width mode and/or a thickness mode, or a combination thereof. Preferably, the PEMS may be capable of length-mode and width-mode detection, which enables more sensitive detection with high peak frequency intensities and minimized damping effects. More preferably, the PEMS is capable of enhanced detection sensitivity using both flexural and longitudinal resonance modes. In an exemplary embodiment, the PEMS may be used at resonance frequencies within the range of about 10 kHz to about 10 GHz.

Additionally, to further increase sensitivity and expedite the detection process, the PEMS may be immersed in a flowing solution for in-liquid detection. The PEMS is preferably situated in a flow cell system to enable tailored, rapid and simultaneous detection and quantification of multiple organic compounds or molecules.

Figure 2A:
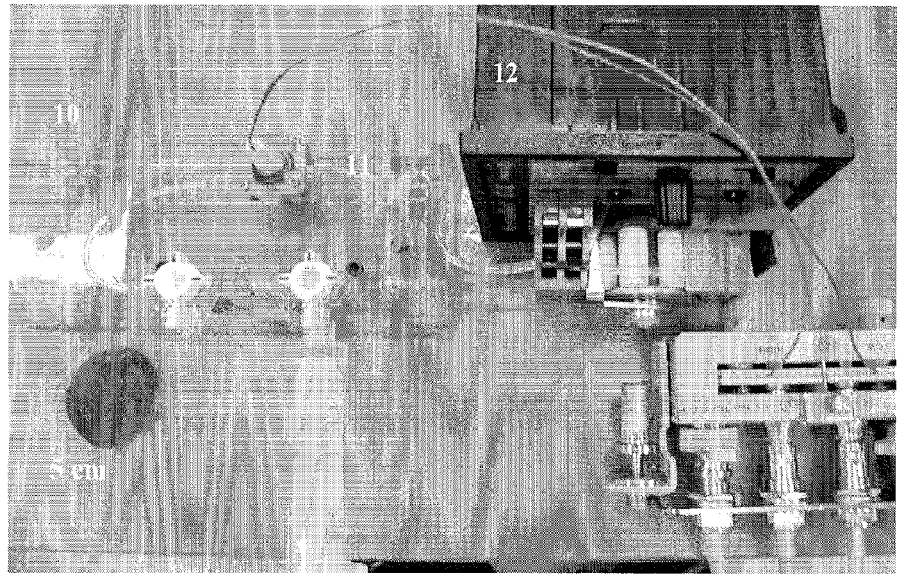
FIG. 2(a) is a flow cell system that can be used in conjunction with the cantilevers of the present invention.
Figure 2B:
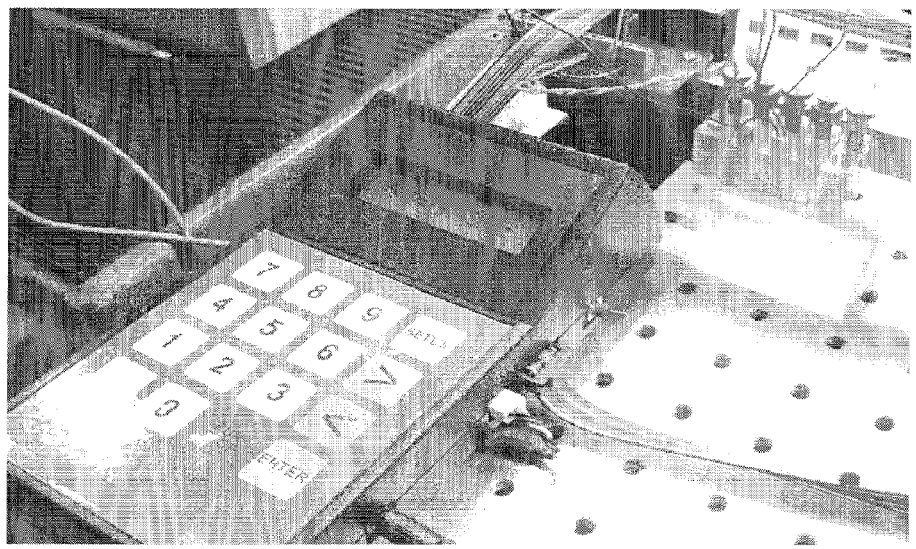
FIG. 2(b) is a 3.5 in by 7.5 in portable PEMS sensor capable of working with 8 sensors and powered by a 9-V battery.

FIG. 2(a) shows a flow cell system 10, with a PEMS holder/measuring unit 11, having a total volume of about 0.03 ml to 10 ml, pump 12, and a mechanism for controlling temperature and humidity (not shown). The flow cell 10 may attain flow rates of 0.01-100 ml/min. The total volume of the flow cell, number of channels and flow rate may vary depending upon the number of compounds to be measured. The flow cell 10 may cooperate with a portable PEMS unit, shown in FIG. 2(b), which has multiple channels for the simultaneous quantification of multiple receptor specific molecules. The portable PEMS is inexpensive and capable of obtaining quick measurements.

These PEMS may be used for various sensing applications such as solid-liquid transition detectors, liquid viscosity and density sensors, mass sensors for in situ and in-water detection. The PEMS may generally be used to detect molecules, compounds, biological elements such as DNA, proteins, viruses, cells, spores, and parasites, or combinations thereof.

The PEMS technology may be particularly useful for the detection of bioterrorism agents. Antibody receptors specific to at least one bioterrorism agent may be bound to an electrode and used to detect the presence of a bioterrorism antigen. In addition to identifying the existence of a bioterrorism agent, it may also be used to quantify the concentration of the agent.

Additionally, PEMS may be useful in the health sciences as a diagnostic instrument. It may be used as a means for early detection of cancers and other diseases. It may also be used to monitor the progress of the disease throughout treatment. The PEMS may be incorporated in a portable device and used as a noninvasive means for testing blood and other bodily fluids for various pathogens, infectious agents and other markers indicative of disease.

PEMS may also be particularly applicable for the food science and food manufacturing industry. PEMS may be used as a diagnostic instrument for detecting pathogens or other disease agents present in food supplies and prepared or processed foods. Additionally, it may also be useful in manufacturing plants and food service industries as a means of intermittently checking food products during different phases of food preparations thereby preventing contamination and the spread of bacterial or viral diseases such as salmonella and *E. coli*.

EXAMPLES

Example 1

Figure 3A:
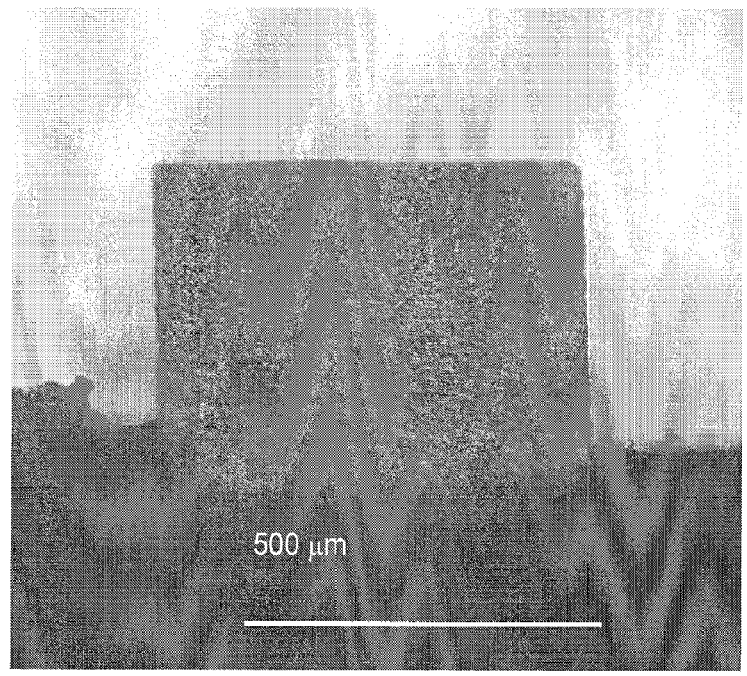
FIG. 3(a) is an optical micrograph of the PEMS.

The effect of a DC bias electric field on the flexural mode resonance frequency shift of a PMN-PT/tin PEMS, having a length of 650±100 µm, a width of 600±50 µm thickness of 14 µm, was investigated for humidity detection. The PEMS was constructed from an 8 µm PMN-PT freestanding film bonded to a 6-µm tin layer by electroplating. Alternatively, the non-piezoelectric layer may be fabricated from copper. A 30 nm thick nickel electrode with a 15 nm thick chromium bonding layer was deposited on one side of the PMN-PT freestanding film by E-beam evaporation (Semicore Equipment, Livermore, Calif.). The tin layer was subsequently electroplated on the nickel electrode and a 150 nm thick gold top electrode was deposited on the other side of the PMN-PT film by evaporation. The PMN-PT/Sn bilayer was then cut and configured as a rectangular strip with a wire saw (Princeton Scientific Precision, Princeton, N.J.). 25-µm thick gold wires (Kulicke & Soffa, Willow Grove, Pa.) were attached to the top and bottom electrodes using conductive glue (XCE 3104XL, Emerson and Cuming Company, Billerica, Mass.). The PMN-PT/Sn strip was then glued to a glass substrate to form a microcantilever, and the PEMS was subsequently subjected to poling at 20 kV/cm and a temperature of 120° C. on a hotplate for 30 minutes. FIG. 3(a) shows an optical micrograph of the fabricated PEMS and top gold electrode.

The performance of the PEMS was first measured without a DC bias electric field at a constant humidity. Subsequently, a DC bias electric field and changes in the relative humidity (RH) were applied to the PEMS system as means to induce stress and change the Young's modulus of the PEMS. The flexural-mode and width-mode resonance frequencies and dielectric constants of the PEMS were measured at different DC bias electric field strengths and at different relative humidity levels. Specifically, examples were carried out under a DC bias electric field varying from about −9 kV/cm to about 9 kV/cm and under relative humidity's of from 60% RH to 30% RH.

Figure 3B:
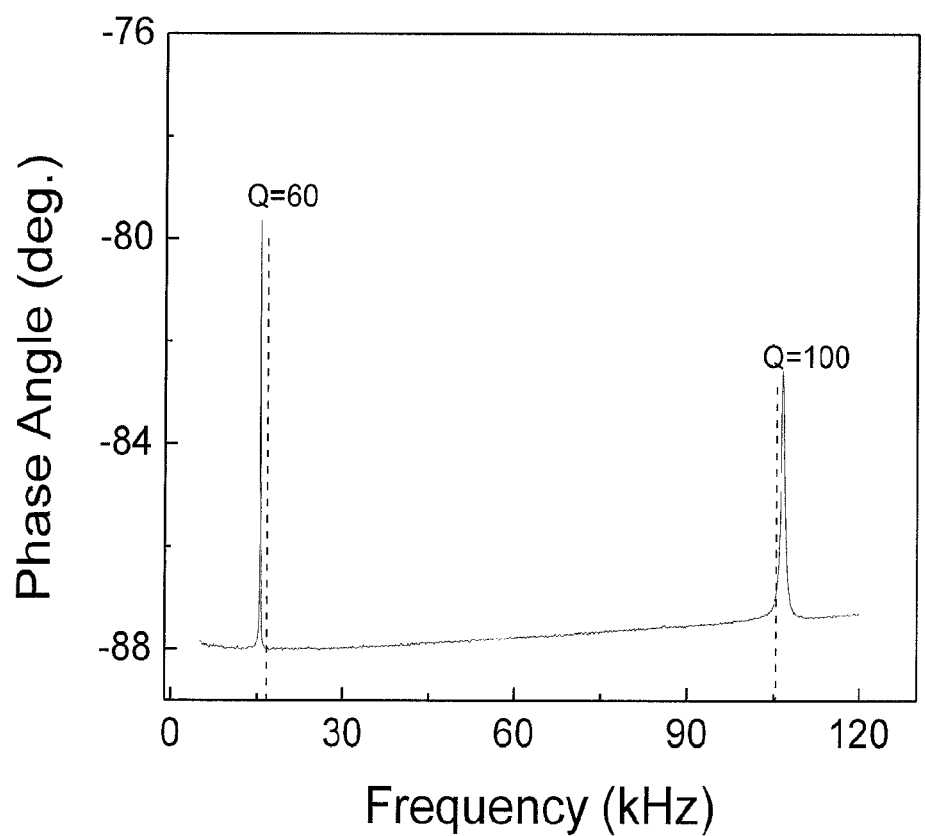
FIG. 3(b) is a graph of phase angle as a function of the frequency flexural resonance spectrum.

FIG. 3(b) shows the characteristics and performance of the PEMS measured in the absence of a DC bias electric field. Specifically, FIG. 3(b) shows the phase angle versus frequency resonance spectrum of the PEMS obtained by an electric impedance analyzer (Agilent 4294A, Agilent, Palo Alto, Calif.). The phase angle, $\theta = \tan^{-1}(\text{Im}(I)/\text{Re}(I))$, represents the angle between the real part, Re(I), and the imaginary part, Im(I), of the complex electrical impedance, I. Off resonance, the PEMS behaved as a capacitor with a phase angle $\theta \cong -90°$. At resonance, the large mechanical vibrations induced a large piezoelectric voltage in phase with the input voltage causing $\theta$ to deviate from −90°. With the known Young's modulus and density of PMN-PT (tin) of $E_p$=80 GPa and $\rho_p$=7.9 g/cm$^3$ ($E_n$=50 GPa and $\rho_n$=7.3 or 9.0 g/cm$^3$), respectively, the theoretical flexural-mode resonance frequencies of the PEMS were calculated and marked by the dashed vertical lines in FIG. 3(b). FIG. 3(b) shows that the PEMS exhibited two flexural frequencies below 120 kHz with Q=60, 100 for the flexural mode and width mode, respectively.

To measure the effects of relative humidity changes on the resonance frequency, the PEMS was placed in a sealed glove box to control relative humidity. A humidifier was then connected to the glove box to first raise the relative humidity (RH) inside the glove box to 90%. Dry air was then circulated in the glove box to establish the desired humidity level. Prior to measuring resonance frequency, the humidity level was allowed to stabilize for period of 5-10 minutes. Throughout the study, the temperature inside the glove box was maintained at 23±0.1° C.

Figure 4A:
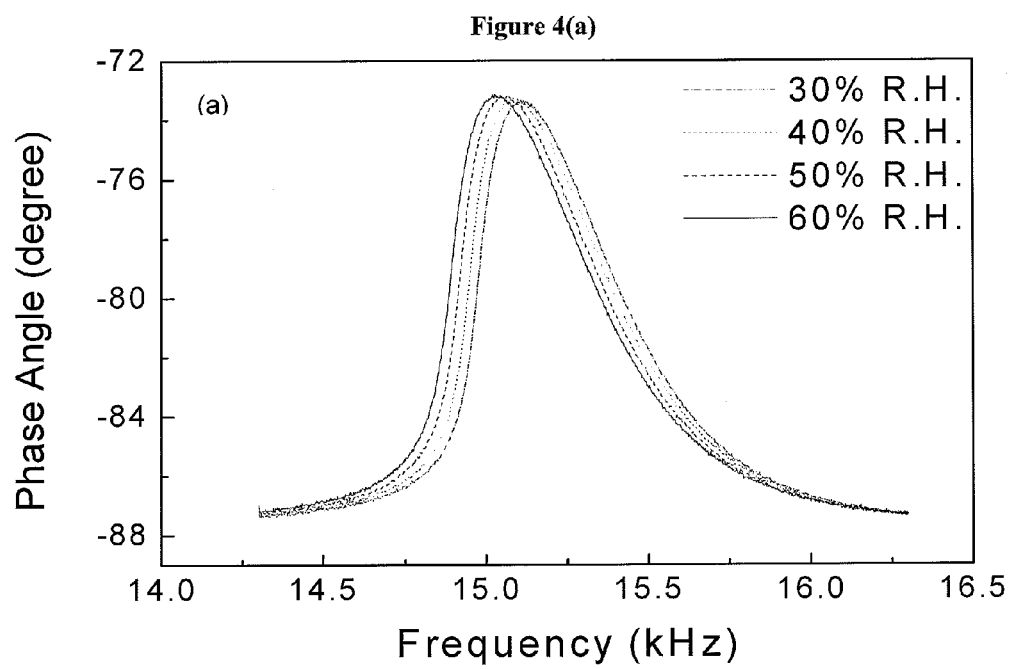
FIG. 4(a) is a graph of phase angle as a function of the frequency resonance spectra at various RH with E=−4 kV/cm and FIG. 4(b) is a graph of relative resonance frequency shift (Δf/f) versus relative humidity at E=−4, 0, and 4 kV/cm.

As an example, FIG. 4(a) shows a graph of phase angle as a function of the resonance frequency spectra of the PEMS at 30%, 40%, 50% and 60% RH with a DC bias electric field of −4 kV/cm. The resonance frequency increased with a decreasing relative humidity due to desorption of water molecules from the sensor surface.

Figure 4B:
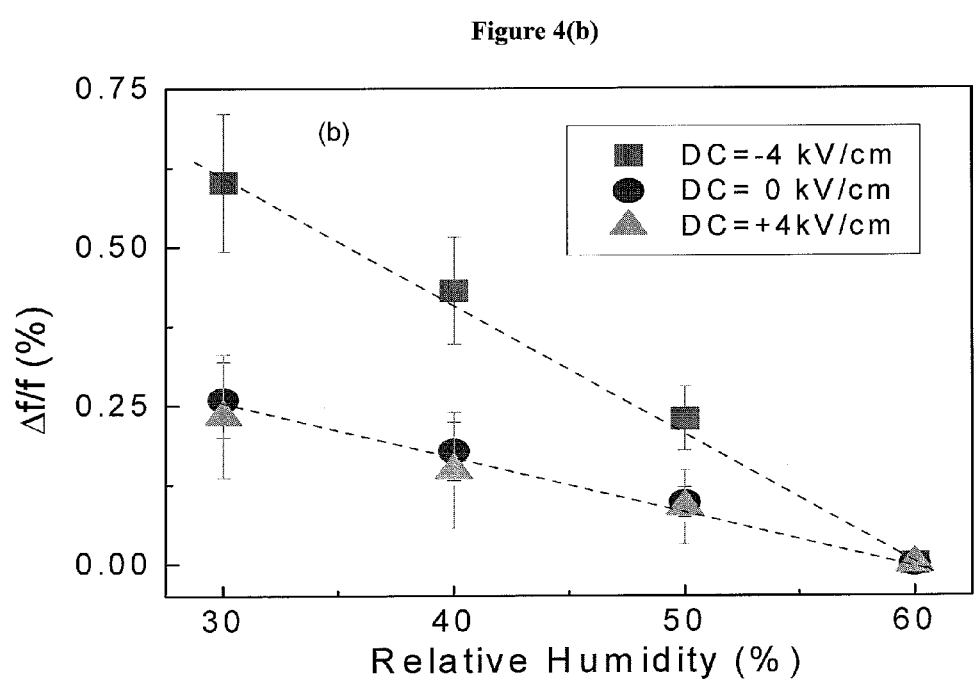

FIG. 4(b) shows a graph of relative resonance frequency shift (Δf/f) versus relative humidity with application of a DC bias electric field of −4, 0 and 4 kV/cm. For purposes of this study, relative frequency shift is defined as the difference in the resonance frequency at a given humidity level in comparison to the resonance frequency at 60% RH, divided by the resonance frequency at 60% RH. As can be seen, from 60% RH to 30% RH, the relative resonance frequency shift was about 0.25% with a DC bias electric field of E=0 and E=4 kV/cm and about 0.63% with E=−4 kV/cm, which is about 2.5 times the shift when compared to E=0 and E=4 kV/cm. The relative resonance frequency shift per relative humidity change at −4 kV/cm was also about 2.5 times that at E=0 and 4 kV/cm. This clearly indicates that the presence of a negative DC bias electric field of about −4 kV/cm significantly enhanced the detection sensitivity of the PEMS.

For purposes of comparison, the relative resonance frequency shift due to the mass change of the PEMS from desorption of water molecules was deduced using the PEMS mass change, $$(\Delta f/f)_{mass} = -\Delta m/2M \quad \text{(Equation 1)}$$

where $\Delta m = (\Delta\Gamma_{Sn} + \Delta\Gamma_{Au})wL$ and $M = (\rho_p t_p + \rho_n t_n)wL$. $\Delta\Gamma_{Sn}$ and $\Delta\Gamma_{Au}$, respectively, denote the water molecule adsorption density change on the tin surface and on the gold surface. w and L represent the width and length of the PEMS, respectively, and $\rho_p = 7.9$ g/cm$^3$ and $t_p = 8$ μm ($\rho_n = 7.3$ g/cm$^3$ and $t_n = 6$ μm) represent the density and thickness of the PMN-PT (tin) layer, respectively. Using two 10 MHz QCMs, one with two gold surfaces and the other with one tin surface and one gold surface, it was found that the mass density changed on the tin surface and on the gold surface from 60% RH to 30% RH, where $\Delta\Gamma_{Sn} = -1.3$ and $\Delta\Gamma_{Au} = -0.4$ ng/mm$^2$, respectively. The deduced relative resonance frequency shift, $(\Delta f/f)_{mass} = 8\times10^{-6}$, was more than 400 times too small to account for the observed resonance frequency shift of $2.5\times10^{-3}$ at E=0 and 4 kV/cm field and more than 800 times smaller than frequency shift of $6.5\times10^{-3}$ at E=−4 kV/cm as shown in FIG. 4(b). These differences show that adsorption of the species of interest changed the Young's modulus of the PMN-PT layer and that application of a negative DC bias electric field further enhanced the change in the Young's modulus providing even better detection sensitivity.

Figure 5A:
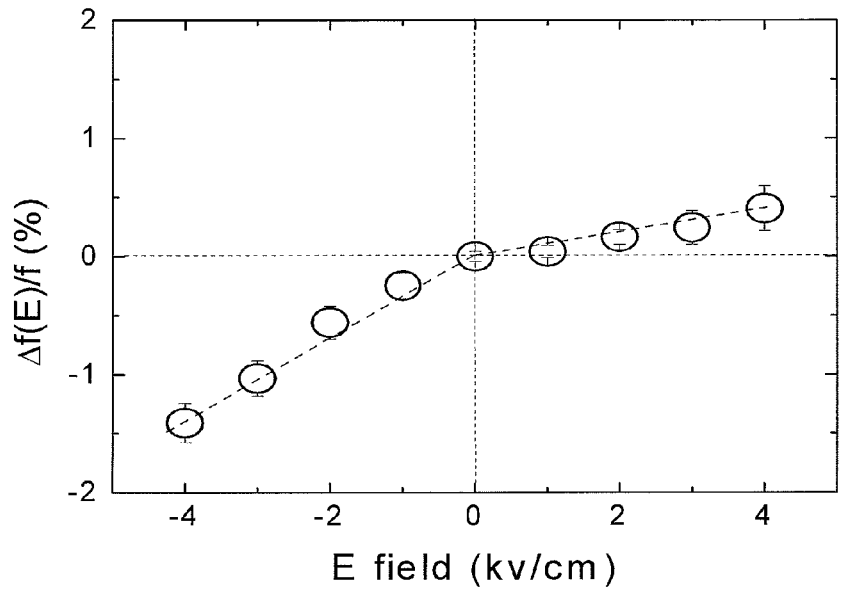
FIG. 5(a) is a graph of $\Delta f(E)/f$ as a function of E, where and $f$ and $\Delta f(E)$ are the resonance frequency at zero DC bias electric field and the change of the resonance frequency at a DC bias electric field E relative to that without a DC bias electric field, respectively.
Figure 5B:
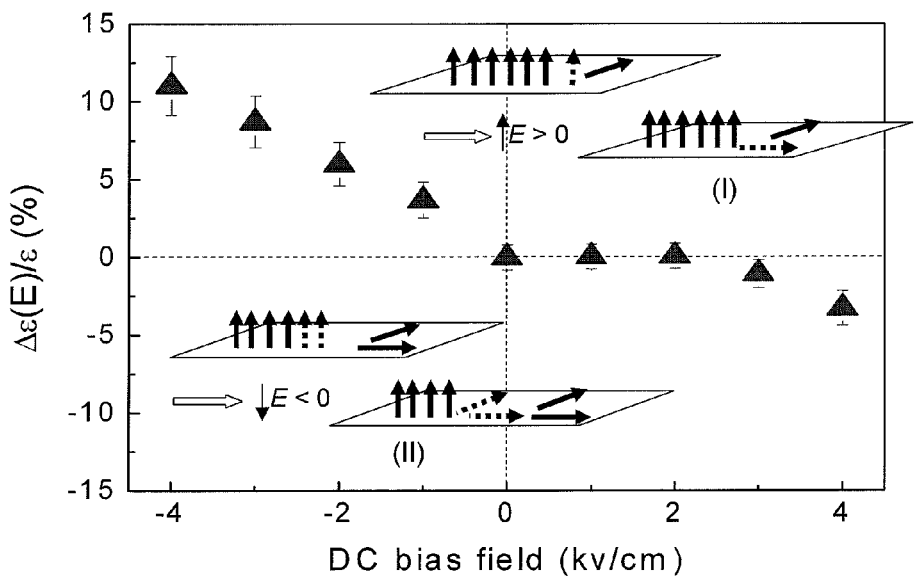
FIG. 5(b) is a graph of $\Delta \in(E)/\in$ as a function of E, where $\in$ and $\Delta \in(E)$ are the dielectric constant at zero DC bias electric field and the change of the dielectric constant at a DC bias electric field E relative to that without a DC bias electric field, respectively.

This phenomenon may be explained by comparing the PEMS resonance frequency measurements. In the absence of relative humidity change, both the flexural resonance frequency and the dielectric constant varied with application of a DC bias electric field. FIGS. 5(a) and 5(b) show the relative resonance frequency shift, $\Delta f(E)/f$, and relative dielectric constant change, $\Delta\in(E)/\in$ as a function of the applied DC bias electric field, E, respectively, where $\Delta f(E) = f(E) - f$, $\Delta\in(E) = \in(E) - \in$ and $f$ and $f(E)$ ($\in$ and $\in(E)$) are the resonance frequencies (dielectric constant) at E=0 an E≠0, respectively. The slope of $\Delta f(E)/f$ at E=−4 kV/cm was about 2.5 times that at E=0 and 4 kV/cm. In addition, $\Delta\in(E)/\in$ was found to be negative for E>0 and positive when E<0. The fact that the dielectric constant decreased with application of an increasing positive DC bias electric field indicated that a positive DC bias electric field switched the polarization from an in-plane direction to the poling direction as schematically shown in I of FIG. 5(b).

The increase in the dielectric as a result of application of an increasingly negative DC bias electric field, indicates that application of a negative DC bias electric field switched the polarization from a vertical direction to an in-plane direction in this field range as schematically illustrated in II of FIG. 5(b). These results indicated that the increase in the in-plane polarization due to application of a negative DC bias electric field of about −4 kV/cm increased the "switchability" of the polarization domains, thereby enhancing the resonance frequency shift in the presence of a negative DC bias electric field. In contrast, a positive DC bias electric field decreased the switch-ability of polarization domains causing a DC bias electric field induced clamping effect.

Example 2

Figure 10:
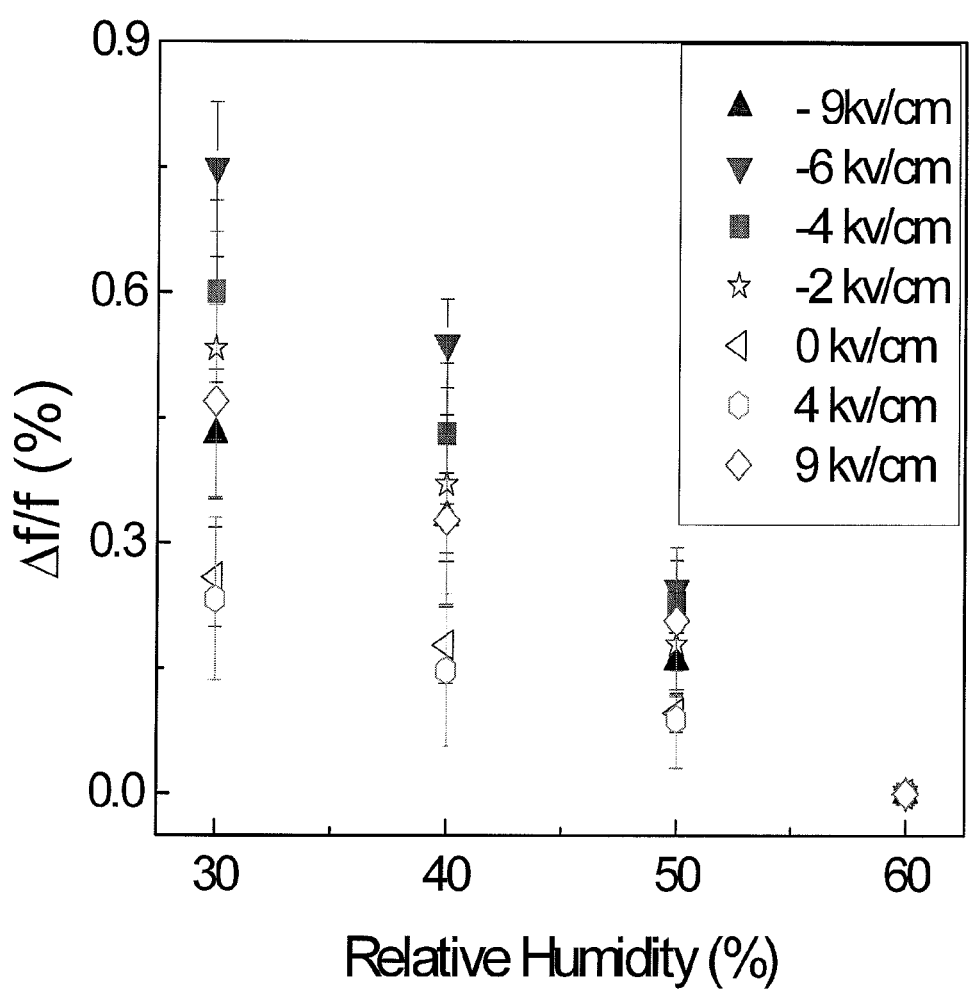
FIG. 10 is a graph of Δf/f as a function of relative humidity under the influence of different DC bias electric fields.

The detection sensitivity of the PEMS was also investigated under application of DC bias electric fields ranging from −9 kV/cm to 9 kV/cm. FIG. 10 shows the relative resonance frequency shift as a function of relative humidity under applied DC bias electric fields ranging from −9 to 9 kV/cm. As can be seen, for relative humidity changes from 60% RH to 30% RH, a DC bias electric field of −6 kV/cm showed the largest resonance frequency shift of any of the applied DC bias fields, including zero.

Figure 11:
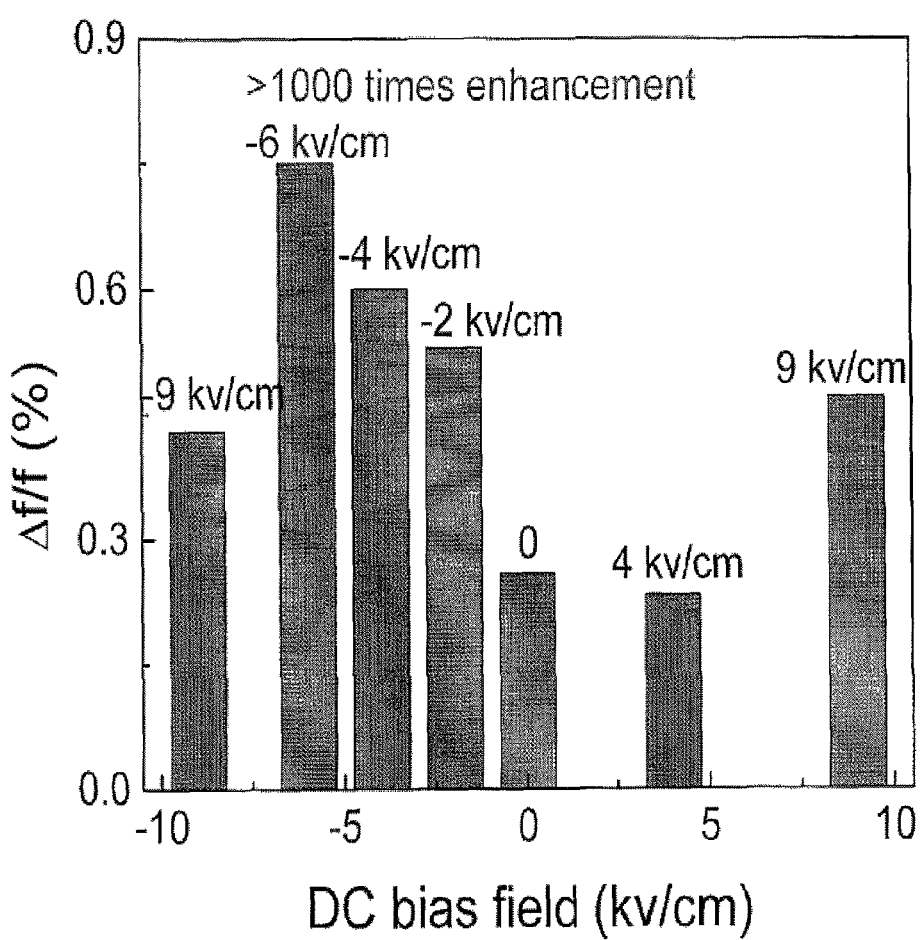
FIG. 11 is a graph of Δf/f as a function of different DC bias electric fields, where Δf/f is the relative resonance frequency shift from 60% relative humidity (RH) to 30% RH.

For comparison, FIG. 11 shows the resonance frequency shift from 60% RH to 30% RH versus the applied DC bias electric field. As shown in FIG. 11, a DC bias field of −6 kV/cm produced a relative resonance frequency shift of 0.75%, three times that of the zero DC bias electric field resonance frequency shift of 0.25%. Note that the 0.75% relative frequency shift with a DC bias electric field of −6 kV/cm was also 1200 times greater than what could be accounted for by mass change alone, $(\Delta f/f)_{mass} = 8\times10^{-6}$.

Example 3

The relationship between a change in Young's modulus and the flexural mode resonance frequency shift was investigated for humidity detection using a PMN-PT/tin PEMS, having a length of 900±100 μm, a width of 700±50 μm and a thickness of 8 μm. The PMN-PT/tin PEMS was constructed from a gold coated 8-μm thick PMN-PT layer bonded to a 6-μm tin layer by electroplating. The two dissimilar surfaces of the PEMS, gold and tin, caused bending during the humidity detection, which was used to quantify detection-induced strain. The PEMS of this example is shown in the insert of FIG. 6(a). To quantify the Young's modulus change in the PMN-PT layer, a separate PMN-PT strip having a length of 900±100 μm, a width of 700±50 μm and a thickness of 8 μm, wherein both sides of the PMN-PT strip are coated with gold, was also employed for humidity detection.

FIG. 6(a) shows the flexural resonance spectra of the PEMS at 20% and 70% relative humidity, as measured by an Agilent 4294A impedance analyzer (Palo Alto, Calif.). The phase angle, $\theta = \tan^{-1}(\text{Im}(I)/\text{Re}(I))$, represents the angle between the real part, Re(I), and the imaginary part, Im(I), of the complex electrical impedance, I. FIG. 6(a) shows that the resonance frequency increased with decreasing relative humidity due to desorption of adsorbed water molecules.

FIG. 6(b) shows the relative resonance frequency shift, $(\Delta f/f)_{RH}$, as a function of relative humidity, where $f$ and $\Delta f$ represent the resonance frequency at 60% RH and the difference in the resonance frequency at a given humidity level in comparison to the resonance frequency at 60% RH, respectively. The subscripts RH, DC and deduced, denote that $\Delta f/f$ was a function of the changes in relative humidity, DC bias electric field.

From 60% RH to 30% RH, it was found that $\Delta\Gamma_{Sn}$=−1.3 and $\Delta\Gamma T_{Au}$=−0.4 ng/mm², respectively. Therefore, $(\Delta f/f)_{mass}$=8×10⁻⁶, which was 400 times too small to account for the observed resonance frequency shift of 2.5×10⁻³ from 60% RH to 30% RH, as shown in FIG. 6(b).

FIG. 6(b) further shows tip displacement as a function of relative humidity. In FIG. 6(b), a negative $d_{RH}$ indicates that the PEMS bent towards the tin side of the PEMS. The PEMS axial tip displacement, $d_{RH}$, was monitored in situ during analyte detection using a LC-2450 laser displacement meter with a 0.5 μm resolution (Keyence). Because $\Delta\Gamma_{Sn}$ was around three times $\Delta\Gamma_{Au}$, the PEMS bent when the relative humidity was changed. Based on the value of $d_{RH}$, it was possible to discern that the average lateral strain, $\in_{ave}$, of the PMN-PT layer was about 4×10⁻⁵, which is about 80 times too small to account for the measured $(\Delta f/f)_{RH}$ shown in FIG. 6(b). Therefore strain did not contribute to the observed enhanced resonance frequency shift.

In a separate study, DC bias electric fields of 1-4 kV/cm were applied to the PEMS while the resonance frequency shift, $(\Delta f/f)_{DC}$, and the tip displacement, $d_{DC}$, were simultaneously measured, where $f$ and $\Delta f$ represent the flexural resonance frequency at E=0 and the difference of the resonance at a given E in comparison to E=0, respectively. As shown in FIG. 6(b), an E>0 denotes an electric field parallel to the poling direction of the PMN-PT layer. For both $(\Delta f/f)_{DC}$ and $d_{DC}$, the effect of decreasing the relative humidity from 60% RH to 30% RH was found to have a similar effect as that of changing E from 0 to 3 kV/cm. Without wishing to be bound by theory, since neither the mass loading effect nor the detection-induced strain accounts for the observed $\Delta f/f$, the similarity between the effect of the change in humidity and the change in the DC bias electric field suggests that both changes in relative humidity and DC bias electric field may cause a change in the Young's modulus of the PMN-PT layer.

Example 4

Figure 7:
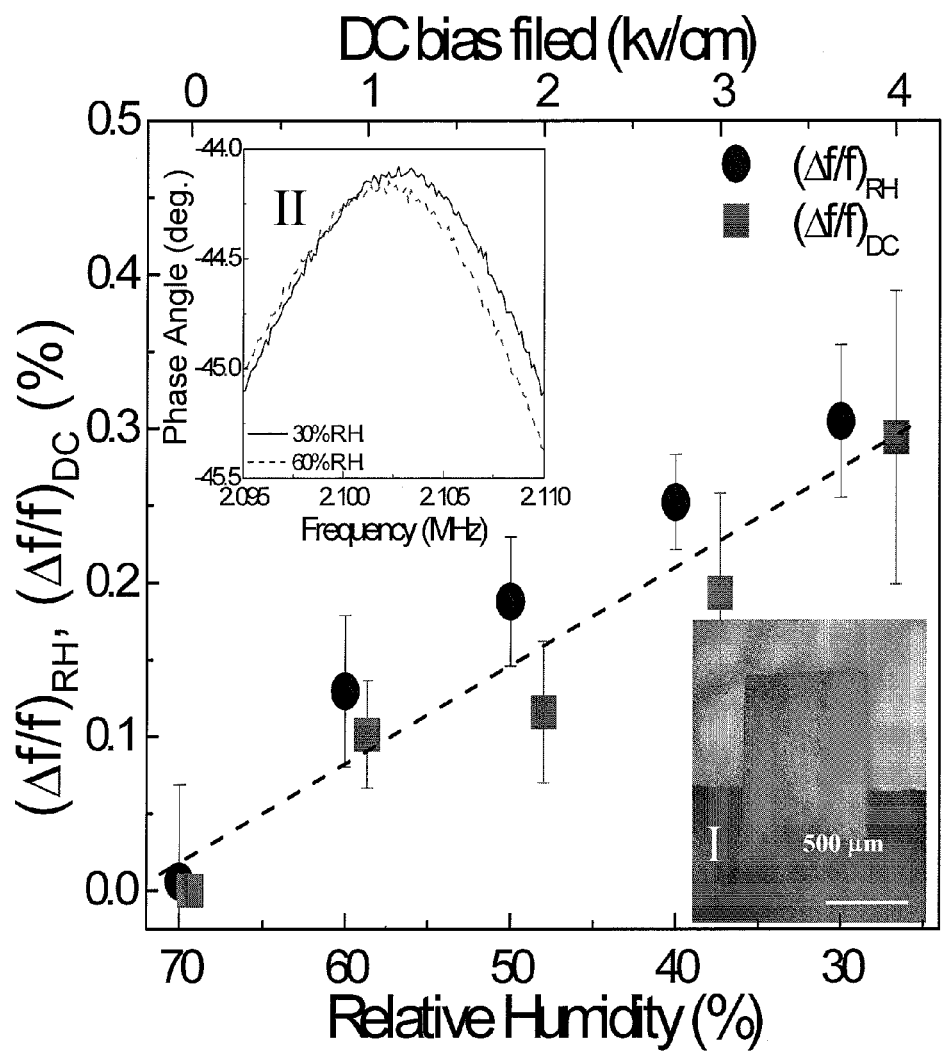
FIG. 7 is a graph of $(\Delta f/f)_{RH}$ as a function of relative humidity and $(\Delta f/f)_{DC}$ as a function of E. The insert figures show a top view of an optical micrograph of the strip and a width-mode resonance spectra at 30% and 60% relative humidity.

To examine whether the Young's modulus of the PMN-PT layer changed during humidity detection, the width mode resonance frequency of a PMN-PT strip having cantilever geometry was investigated. To ensure that the lateral stress of the PMN-PT strip did not change signs across its thickness, the PMN-PT strip was coated with two identical gold surfaces, such that no bending occurred in the PMN-PT strip during humidity detection. Additionally, the PMN-PT strip did not include a non-piezoelectric layer; therefore, it did not exhibit a flexural-mode resonance peak. Insert I of FIG. 7 shows an optical micrograph of the PMN-PT strip and Insert II of FIG. 7 shows the first width-mode resonance spectra of the PMN-PT strip at 30% RH and 60% RH. As can be seen from the inserts in FIG. 7, the width-mode resonance frequency changed with the relative humidity.

FIG. 7 shows that the width mode resonance of the PMN-PT strip shifted with changing relative humidity levels. The increasing $(\Delta f/f)_{RH}$ with decreasing relative humidity indicated that the lateral Young's modulus of the strip changed as a result of changes in relative humidity. Furthermore, the PMN-PT width mode and flexural mode resonance frequencies appear to be similar since both the width mode and flexural mode resonance frequency shifts increased with decreasing relative humidity levels.

FIG. 7 also shows the width mode resonance frequency shift of the PMN-PT strip when subjected to a DC bias electric field. The resultant width mode resonance frequency shift shows that the effect of a positive E was similar to that of a decreasing relative humidity.

The width mode resonance frequency, $f_w$, is related to the lateral Young's modulus, $Y_p$, as shown in Equation 2, $$f_w = (Y_p/\rho_p)^{1/2}/2w, \quad \text{(Equation 2)}$$

where $\rho_p$ and w represent the density and width the PMN-PT strip.

Because $$\frac{\Delta f_w}{f_w} \ll 1$$

and because the width change was negligible, the relative change in the Young's modulus may be expressed as Equation 3.

$$\left(\frac{\Delta Y_P}{Y_P}\right)_{strip} \cong 2\frac{\Delta f_w}{f_w} \quad \text{(Equation 3)}$$

The relative Young's modulus change of the PMN-PT layer therefore was calculated according to Equation 5.

Figure 8:
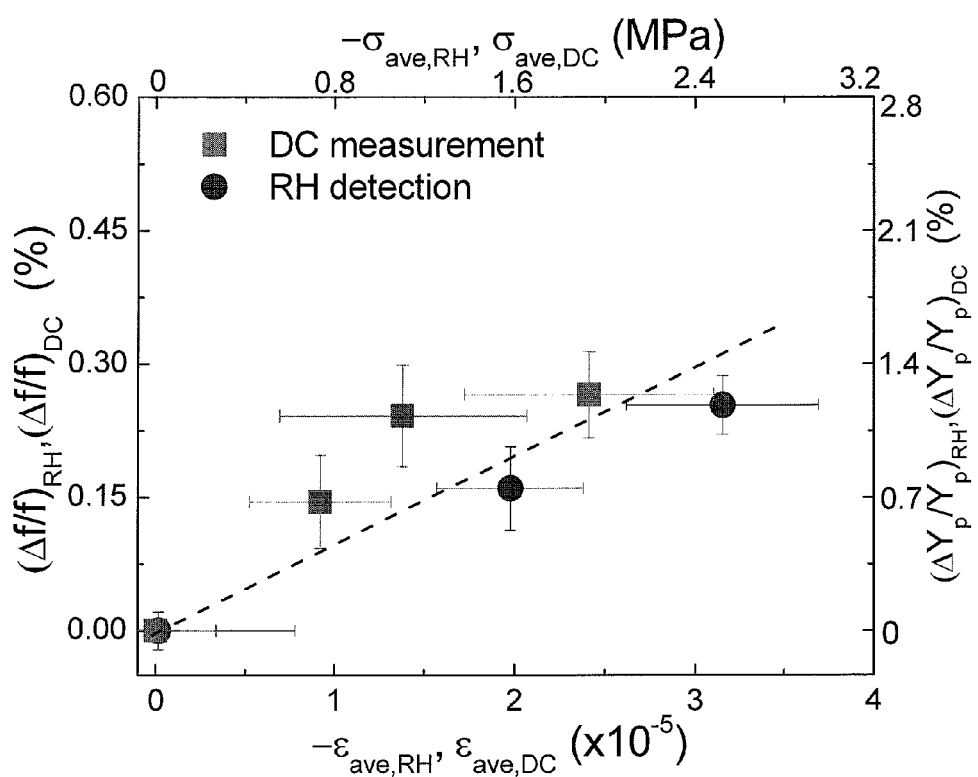
FIG. 8 is a graph of $\Delta f/f$ and deduced $\Delta Y_p/Y_p$ as a function of $-\in_{ave}$ and $-\sigma_{ave}$ for various relative humidity detection (solid circles) and various DC bias field measurements (solid squares), respectively.
Figure 9:
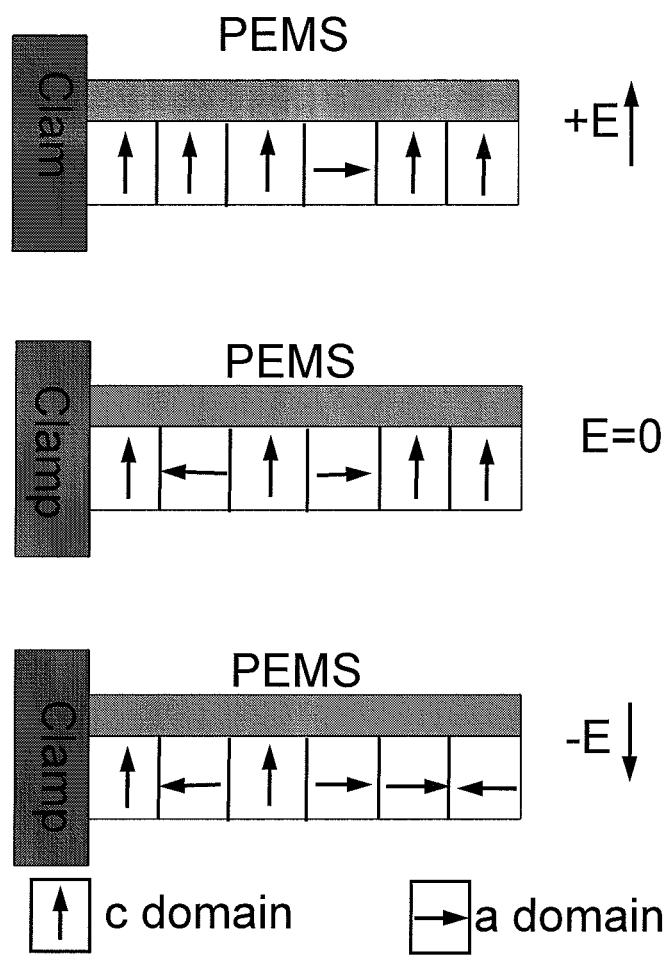
FIG. 9 illustrates polarization domain switching.

Without wishing to be bound by theory, the deduced change in the Young's modulus of the PMN-PT layer appears to validate that the Young's modulus change was the underlying mechanism for the PEMS flexural-mode resonance frequency shift during the humidity detection. As shown in FIG. 6(b), the deduced $\Delta f/f$ as a function of relative humidity overlapped with the experimental results. FIG. 8 further confirms that the flexural resonance frequency shift, which provides enhanced detection sensitivity, is induced by a change in the Young's modulus of the PMN-PT layer. FIG. 8 shows $(\Delta f/f)$ as a function of average bending strain, $-\in_{ave}$, at the outer surface of the PMN-PT layer, which is calculated from the axial tip displacement of FIG. 6(b). The relative resonance frequency shift correlated with the lateral strain regardless of whether the resonance frequency shift was caused by a DC bias electric field or by a change in humidity. Additionally, by comparing FIGS. 6a-8, the change in the Young's modulus appears to be caused by non-180° polarization domain switching as polarization domain pattern changes were observed in piezoresponse force microscopy (PFM). A schematic of the polarization domain switching in a DC electric field is shown in FIG. 9. For comparison, the average stresses in the PMN-PT layer due to the adsorption or desorption of water molecules and due to application of a DC bias electric field were estimated as $\sigma_{ave,RH}=Y_p\in_{ave,RH}$ and $\sigma_{ave,DC}=Y_p\in_{ave,DC}$, respectively. FIG. 8 shows that both $\sigma_{ave,RH}$ and $\sigma_{ave,DC}$ were on the order of MPa and the relative Young's modulus change was about 0.5% per MPa stress in the PMN-PT layer, which was comparable to the 1-1.5% Young's modulus change per MPa stress reported for unpoled lead zirconate titanate (PZT). Without wishing to be bound by theory, it appears that the stress effect can induce much larger frequency shifts than predicted by mass loading in chemical and biological detection because surface stress causes a change in the Young's modulus, inducing a change in the spring constant of the PEMS. Furthermore, a change in the Young's modulus may be induced by non-180° polarization domain switching due to analyte binding and/or by application of a DC bias electric field.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

The invention claimed is:

1. A method for using a piezoelectric sensor comprising the steps of:
    inducing a change in the Young's modulus of a piezoelectric layer by non-180° polarization domain switching in said piezoelectric layer of the piezoelectric sensor, and
    detecting a species of interest by measuring a frequency shift of said piezoelectric layer having a changed Young's modulus, wherein said frequency shift is caused by binding of said species of interest to receptors on said piezoelectric sensor.

2. A method as claimed in claim 1, wherein said detecting step is carried out with application of a DC bias electric field to said piezoelectric sensor.

3. The method claim 2, wherein the DC bias electric field is from about −20 kV/cm to about 20 kV/cm.

4. The method claim 1, wherein the piezoelectric layer is selected from the group consisting of PZT, PMN-PT and NKN-LN.

5. The method claim 1, wherein the piezoelectric layer has a thickness of from about 0.5 μm to about 250 μm.

6. The method claim 1, wherein the piezoelectric layer has a thickness of from about 0.5 μm to about 127 μm.

7. The method claim 1, wherein the piezoelectric layer has a thickness of from about 0.5 μm to about 100 μm.

8. The method claim 1, wherein the piezoelectric layer has a piezoelectric coefficient $-d_{31}$ of about 20 pm/V to about 5000 pm/V.

9. The method claim 1, wherein the piezoelectric layer has a piezoelectric coefficient $-d_{31}$ greater than about 20 pm/V.

10. The method claim 1, wherein the piezoelectric layer has a piezoelectric coefficient $d_{33}$ greater than about 40 pm/V.

11. The method claim 1, wherein the piezoelectric sensor further comprises an electrical insulation layer which enables the sensor to substantially withstand liquid damping.

12. The method claim 1, wherein the piezoelectric sensor may further comprise a non-piezoelectric layer selected from the group consisting of: a metal, a ceramic and a plastic layer.

13. The method claim 1, wherein during the detection step the piezoelectric sensor is operated in a mode selected from the group consisting of: flexural mode and longitudinal mode.

14. The method claim 13, wherein during the detection step, the piezoelectric sensor is operated in a longitudinal mode selected from the group consisting of: length mode, width mode or thickness mode.

15. The method claim 2, wherein the DC bias electric field is from about −10 kV/cm to about 10 kV/cm.

16. The method of claim 1, wherein said change in the Young's modulus is from about 25% to about 70%.

17. The method of claim 16, wherein said change in the Young's modulus is induced by binding of the species of interest to receptors on said piezoelectric sensor.

18. The method of claim 1, wherein the piezoelectric sensor is a piezoelectric microcantilever sensor.

19. The method of claim 1, wherein the sensor is immersed in a flowing liquid during said detecting step.

20. The method of claim 9, wherein the piezoelectric layer has a piezoelectric coefficient $d_{33}$ greater than about 40 pm/V, and a thickness of from about 0.5 μm to about 250 μm.

21. The method of claim 20, wherein said detecting step is carried out with application of a DC bias electric field to said piezoelectric sensor.

22. The method claim 21, wherein the DC bias electric field is from about −20 kV/cm to about 20 kV/cm.

* * * * *